United States Patent [19]

Pall et al.

[11] Patent Number: 4,880,548
[45] Date of Patent: Nov. 14, 1989

[54] DEVICE AND METHOD FOR SEPARATING LEUCOCYTES FROM PLATELET CONCENTRATE

[75] Inventors: David B. Pall, Roslyn Estates; Thomas C. Gsell, Glen Cove, both of N.Y.

[73] Assignee: Pall Corporation, Glen Cove, N.Y.

[21] Appl. No.: 185,993

[22] Filed: Apr. 25, 1988

Related U.S. Application Data

[63] Continuation-in-part of Ser. No. 156,894, Feb. 17, 1988, abandoned.

[51] Int. Cl.⁴ .............................................. B01D 39/04
[52] U.S. Cl. .................... 210/767; 210/435; 210/504; 210/508
[58] Field of Search .............. 210/651, 767, 435, 446, 210/506, 507, 508, 503, 504, 505, 648

[56] References Cited

U.S. PATENT DOCUMENTS

| | | | |
|---|---|---|---|
| 3,448,041 | 6/1969 | Swank | 210/23 |
| 3,593,854 | 7/1971 | Swank | 210/436 |
| 3,765,536 | 10/1973 | Rosenberg | 210/446 |
| 3,905,905 | 9/1975 | O'Leary et al. | 210/436 |
| 3,935,110 | 1/1976 | Schmid et al. | 210/445 |
| 3,935,111 | 1/1976 | Bentley | 210/446 |
| 3,954,621 | 5/1976 | Etani et al. | 210/314 |
| 4,009,714 | 3/1977 | Hammer | 128/214 |
| 4,009,715 | 3/1977 | Forberg et al. | 128/214 |
| 4,087,363 | 5/1978 | Rosemeyer et al. | 210/315 |
| 4,092,246 | 5/1978 | Kummer | 210/65 |
| 4,116,845 | 9/1978 | Swank | 210/446 |
| 4,246,107 | 1/1981 | Takenaka | 210/806 |
| 4,283,289 | 8/1981 | Meyst et al. | 210/448 |
| 4,330,410 | 5/1982 | Takenaga et al. | 210/767 |
| 4,416,777 | 11/1983 | Kuroda et al. | 210/446 |
| 4,422,939 | 12/1983 | Sharp et al. | 210/445 |
| 4,477,575 | 10/1984 | Vogel et al. | 436/170 |
| 4,534,757. | 8/1985 | Geller | 604/85 |
| 4,617,124 | 10/1986 | Pall et al. | 210/638 |
| 4,618,533 | 10/1986 | Steuck | 428/315 |
| 4,636,312 | 1/1987 | Willis | 210/416.1 |
| 4,701,267 | 10/1987 | Watanabe et al. | 210/806 |
| 4,702,947 | 10/1987 | Pall et al. | 210/508 |

FOREIGN PATENT DOCUMENTS

| | | |
|---|---|---|
| 0045476 | 2/1982 | European Pat. Off. . |
| 0155003 | 9/1985 | European Pat. Off. . |
| 0267286 | 5/1988 | European Pat. Off. . |
| 2222951 | 7/1974 | Fed. Rep. of Germany . |
| 2735179 | 9/1976 | Fed. Rep. of Germany . |
| 2239282 | 7/1974 | France . |
| 2017713 | 1/1979 | Japan . |
| WO87/05812 | 10/1987 | Japan . |

*Primary Examiner*—W. Gary Jones
*Attorney, Agent, or Firm*—Leydig, Voit & Mayer

[57] ABSTRACT

A device for the depletion of the leucocyte content in a platelet concentrate, preferably comprising a modified porous, fibrous medium with a critical wetting surface tension of at least about 90 dynes/cm and a method for the depletion of the leucocyte content and platelet concentrate comprising passing the platelet concentrate through the porous medium.

94 Claims, 5 Drawing Sheets

4,880,548

DEVICE AND METHOD FOR SEPARATING LEUCOCYTES FROM PLATELET CONCENTRATE

This application is a continuation-in-part of U.S. application Ser. No. 07/156,894 filed Feb. 17, 1988, now abandoned.

TECHNICAL FIELD

This invention relates to a method for reducing the leucocyte content of platelet concentrate derived from blood, particularly of platelet concentrate derived from human blood, and a device for effecting that separation.

BACKGROUND OF THE INVENTION

The development of plastic blood collection bags in the 1960's facilitated the separation of donated whole blood into its various components, thereby making platelet concentrates available as a transfusion product. The separation of a single unit of donated whole blood, about 450 ml in USA practice, into its components is accomplished by use of differential sedimentation. The unit of whole blood is collected in a plastic blood collection bag with integral satellite transfer bags, and is separated by centrifugation into red cell concentrate and platelet rich plasma. The platelet rich plasma is transferred to an empty attached satellite bag, and the sedimented red cells are sparated from the collection system. The platelet rich plasma is centrifuged at an increased G force which divides it into platelet concentrate (PC) and platelet poor plasma, which are separated by transfer to a satellite bag. The final PC should contain on average not less than $5.5 \times 10^{10}$ platelets in 50 to 70 ml of plasma, or approximately $10^6$ platelets per microliter ($\mu$l). The component separation must take place within 6 hours of whole blood collection. One unit of platelet concentrate usually increases the platelet count of a 70 kg individual by 5000–10,000/$\mu$l. The usual dose administered to a thrombocytopenic adult ranges from 6–10 units of concentrate.

Platelets can also be prepared using a specialized blood component collection procedure called apheresis. Using a variety of continuous or discontinuous flow devices, platelets are collected from a single donor. With this method, whole blood is removed from the donor, and centrifuged by ex-vivo technique into its component parts. The desired component, platelets in this instance, is harvested and the remainder of the autologous blood is returned to the donor. This procedure allows collection of multiple units from one donor. Typically the 2 to 3 hour apheresis procedure will produce a platelet product containing $3 \times 10^{11}$ platelets, equivalent to 6–8 units of random donor platelets. Donors providing single-donor platelet concentrates are usually HLA-matched to the recipient. Single-donor platelets are generally given to patients who are immunologically unresponsive to transfusions of random donor platelet concentrates, or to individuals who are considered to be candidates for bone marrow transplantation.

Platelets serve two major functions in maintaining hemostasis. First, they adhere to injured blood vessel walls, aggregate and form a hemostatic plug. Second, they participate in fibrin formation by releasing platelet factor 3 and promoting coagulation factor mediated hemostasis. Platelets also release vasoactive amines, cationic proteins, nucleotides and enzymes, as well as thromboxane $A_2$ which induces vasoconstriction, and promotes platelet aggregation via its inhibitory effect on cyclic AMP formation.

Platelet transfusions are indicated for treatment of bleeding due to thrombocytopenia secondary to inadequate production of platelets by the bone marrow, a condition known as amegakaryocytic thrombocytopenia. This bone marrow hypoplasia may be due to chemotherapy, tumor invasion or primary aplasia. For example, a patient with acute leukemia may be thrombocytopenic at diagnosis or become thrombocytopenic secondary to chemotherapy or radiation procedures. Patients with adequate numbers of platelets but abnormal congenital platelet function may have a range of responses resulting in mild to severe hemorrhagic disease, for example Glanzmann's Thrombasthenia. Patients may also experience platelet functional disorders secondary to a plasma abnormality, such as von Willebrand's disease or uremia. Platelet transfusions may also be used in patients with thrombocytopenia associated with massive blood replacement secondary to trauma, or for patients undergoing surgical procedures necessitating large amounts of blood like open heart surgery. Patients who have ingested aspirin may also demonstrate a transient platelet dysfunction and require platelet transfusion support for emergency surgical procedures.

The use of platelet concentrates has and continues to rapidly increase. This is demonstrated by the last survey conducted by the American Blood Commission. This survey indicates that the national use of platelet concentrates increased from 0.41 million in 1971 to 2.86 million in 1980, a 6 fold increase. By contrast, the use of packed red cells during the same period went from 6.32 million to 9.99 million units, only a 1.5 fold increase. Random donor platelets were being prepared from less than 6 percent of the whole blood units collected in 1971 compared to almost 20 percent in 1980. The proportion of donated whole blood units used to prepare platelet concentrates in 1987 is approximately 70–80 percent. Future demands may exceed the available blood supply, and, indeed, present demand already does so in some localities.

There are several reasons for this accelerated platelet use, including more aggressive use of chemotherapy with resultant prolonged periods of bone marrow aplasia. The availability of platelet components and more aggressive use of platelet transfusion permit the use of these aggressive chemotherapy programs.

The transfusion of platelet concentrate is not without risk for those patients receiving both acute and chronic transfusion support. Chills, fever and allergic reactions may occur in patients receiving acute as well as chronic platelet therapy. Repeated platelet transfusions frequently leads to alloimmunization against HLA antigens, as well as platelet specific antigens. This in turn decreases responsiveness to platelet transfusion. Leucocytes contaminating platelet concentrates, including granulocytes and lymphocytes, are associated with both febrile reactions and alloimmunization leading to platelet transfusion refractoriness. Another life-threatening phenomenon affecting heavily immunosuppressed patients in Graft versus host disease. In this clinical syndrome, donor lymphocytes transfused with the platelet preparations can launch an immunological reaction against the host, i.e. the transfusion recipient, with pathological consequences. Another potential consequence of platelet transfusion is the transmission of bacterial, viral, and parasitic infectious diseases.

Growing evidence suggests that leucocyte depleted platelet concentrates decrease the incidence of febrile reactions and platelet refractoriness. Leucocyte depleted blood components should also be evaluated for a potential role in reducing the potential for Graft vs. host disease. Leucocyte depletion of platelet preparations may also diminish the transmission of certain viruses (e.g. AIDS and CMV).

Platelet preparation contain varying amounts of leucocytes. Platelet concentrates prepared by the differential centrifugation of blood components will have varying leucocyte contamination related to the time of centrifugation and G force used. Leucocyte contamination is also influenced by the choice of apheresis technique used to harvest the component. While the dose of contaminating leucocytes necessary to cause a febrile reaction or elicit platelet refractoriness in repeated transfusion remains unknown, Stec et.al (Stec, N., Kickler, T. S., Ness, P. M. and H. G. Braine, Effectiveness of Leukocyte (WBC) Depleted Platelets in Preventing Febrile Reactions in Multi-Transfused Oncology Patients, American Association of Blood Banks, San Francisco, (Abstract No. 598), Nov. 3–7, 1986) and Dan and Stewart (Dan, M. E., and Stewart, S., Prevention of Recurrent Febrile Transfusion Reactions Using Leukocyte Poor Platelet Concentrates Prepared by the "Leukotrap" Centrifugation Method, American Association of Blood Banks, San Francisco, (Abstract No. 597), Nov. 3–7, 1986) have demonstrated that leucocyte removal efficiencies of 81 to 85% are sufficient to reduce the incidence of febrile reactions to platelet transfusions. Several other recent studies report a reduction in alloimmunization and platelet refractoriness at levels of leucocyte contaminaton $<1\times10^7$ per unit. The level of leucocyte contamination in conventional platelet preparations is generally at a level $\geq \times 10^8$. The existing studies, therefore, suggest at least a two log (99%) reduction of leucocyte contamination is required. More recent studies suggest that a three log (99.9%) or four log (99.99%) reduction would be significantly more beneficial. An additional desired criterion is to restrict platelet loss to about 15% or less of the native platelet concentrate.

Centrifugal methods are available which reduce the number of leucocytes contaminating platelet preparations. These methods have often proved unsatisfactory because they result in an unaccpetable platelet loss. Centrifugation in conjunction with the use of specially constructed pooling bags reduces the concentration of leucocytes by approximately a single log. The technique is expensive and labor intensive.

The use of laboratory filters to remove contaminating leucocytes from platelet preparations has in some instances yielded 2 log leucocyte removal efficiencies with platelet recoveries averaging 90%, however, in most studies employing laboratory filters, unacceptably high platelet losses have been reported. The experience with the use of laboratory filters to deplete platelet preparations of leucocytes has shown the procedures to be inconsistent in their performance. Further, the use of these devices is labor intensive and results in reduced shelf life for a unit of conventionally collected platelets. Because of the reduced shelf life, those units are not recommended for bedside use.

Characteristics Desirable in a Leucocyte Depletion Device

The ideal device for the depletion of leucocytes from platelet preparations should be readily available, inexpensive, designed for use at bedside, and be capable of delivering the platelet components to the patient within 30 seconds of the initiation of the transfusion of the platelet preparation. The leucocyte content of the platelet preparation should be reduced by the device by at least 99% or to a total no greater than $5\times10^6$ leucocytes per administration and preferably by 99.9% or more to a level less than $5\times10^5$ leucocytes per administration. After infusion into a patient, platelet function should be only minimally affected, and platelet survival time within the new host should be close to normal. Further, because of the high cost and increased demand for platelet preparations, as well as the clinical need to deliver a maximum therapeutic dose, this ideal device should deliver the highest possible proportion of the platelets originally present in the bag. Such a device is an object of this invention.

Devices which have previously been used in attempts to meet this objective have been based on the use of packed fibers, and have generally been referred to as filters. In describing this invention, the terms depletion device, element, assembly, filter, and filter-adsorber are used interchangeably.

Recovery of Platelets

Platelets are notorious for being "sticky", an expression reflecting the tendency of platelets suspended in blood plasma to adhere to any non-physiological surface to which they are exposed. Under any circumstances, they also adhere strongly to each other.

Platelets are also sensitive to a variety of environmental stimuli, one of which is exposure to cold. Whereas in blood banking practice other blood components are stored at 4° C. or less in order to extend their useful life, platelets are best preserved at normal indoor ambient temperature, e.g. 20° to 22° C. At this temperature their nominal useful life in U.S. practice is 5 days, although many physicians prefer to use them within 2 or 3 days of collection.

Whereas the number of red cell concentrate units normally infused into to a patient is one per administration, the common practice with respect to platelet concentrate is to transfuse a pool of six to ten units of platelets per administration, containing a total of about 300 to 700 ml of platelet concentrate.

Based on 1987 prices, in dollars, a 1% improvement in platelet recovery translates into value gained well in excess of about four dollars. In non-monetary terms, high efficiency of recovery is important because platelet concentrate is often in short supply.

An objective of this invention is a leucocyte depletion device having the highest possible platelet recovery.

Recovery of platelets may be adversely affected in several ways:

(a) The platelets may adhere to the surfaces of components of the leucocyte depletion device. If the device depends on filtration or adsorption as a mechanism for removal of leucocytes, the filter internal surface area (e.g., the surface area of the fibers in a fibrous filter, or fiber surface area) will be substantial, of the order of one or more square meters, and adhesion of platelets to the fiber surfaces tends to cause substantial, and often near complete removal of platelets.

(b) Platelet concentrate present within the leucocyte depletion device at the completion of the transfusion will be lost. For this reason, the internal volume of the device should be as small as is consistent with obtaining the desired degree of leucocyte depletion.

(c) The internal volume of ancillary parts of the apparatus, including the tubing and drip chamber should also be as small as possible.

The leucocyte depletion device of this invention directly and effectively minimizes loss due to the above listed causes.

Viability of Platelets After Leucocyte Depletion

In any system which depends upon filtration to remove leucocytes, there will be substantial contact between platelets and the filter internal surfaces. The filter must be such that the platelets are not adversely affected by that contact. Such a filter is an objective of this invention.

Capacity

As separated from whole blood in current blood banking practice, platelet concentrate contains not only a large proportion of the leucocytes present in the native blood, but also may contain fibrinogen, fibrin strands, tiny fat globules, some red cells, and other components normally present in small proportions.

During the centrifuging process which concentrates the platelets and partially separates them from the remaining components, there is a tendency for microaggregates to form. These may comprise some platelets together with leucocytes, red cells, fibrin, and other components. Gels, which may be formed by fibrinogen and/or fibrin, are present in a significant proportion of platelet concentrate prepared using U.S. approved blood banking methods.

Platelet concentrate (PC) is stored with continuous gentle mixing at about 20°-22° C., for use within a period of 5 days. Mixing prevents agglomeration and encourages gas exchange, thereby controlling pH, and bathes the product in needed nutrients. Nevertheless, the number and size of microaggregates increase with time. Further, gel-like bodies may be formed, which may comprise fibrinogen, degenerated protein, and degenerated nucleic acids.

If the leucocyte depletion device comprises a porous structure, microaggregates and gels tend to collect on or within the pores, causing blockage which inhibits flow. Normally, transfusions use gravity, developing no more than about 0.1 to 0.14 kg/cm$^2$ to induce flow from the storage bag through the leucocyte removal device to the patient. For this reason a particularly important characteristic of a separation device is its resistance to clogging.

Because of the unusual and highly variable combination of clogging factors, the experience of a person skilled in the art of filter design is inadequate when applied to removal of undesirable components from platelet concentrate, and novel, inventive approaches have been required to design a filter which efficiently retains leucocytes, allows a high percentage of the platelets to pass, and will reliably pass up to ten units of platelet without clogging. The development of such a device is an objective of this invention.

Ease and Rapidity of Priming

Ease of use is an important characteristic of any leucocyte depletion system. As noted above, for leucocyte depletion devices ease of priming is a particularly important factor. The term priming refers to start-up flow of platelet concentrate from the bag through the filter to the patient. A short priming period is always desirable to conserve nurse/technician time. An objective of this invention is to keep that time to below about 10 seconds when the PC bag is hand squeezed, and below about one minute when primed by gravity.

Preconditioning of Leucocyte Depletion Devices Prior to Priming

A number of devices in current use require pretreatment prior to passing PC, usually consisting of passing physiological saline, some of which may be delivered to the patient's vein. The necessity for such an operation is clearly very undesirable for the reasons set out in the preceding section. The reasons for using such pretreatments vary. They include removal of acid hydrolysate developed during steam sterilization of devices containing cellulose acetate fibers, assurance of freedom from foreign solids which may be present in natural fibers, and prevention of hemolysis (loss of the integrity of red blood cells with subsequent loss of their contents to the external milieu) if the fibers are hygroscopic. When synthetic fibers are used, passing saline as a first step helps to ease problems due to the poor wettability of synthetic fibers, which can result in portions of the fibrous medium remaining unwetted during the leucocyte depletion process. If significant portions of the medium remain unwetted, pressure drop is higher and less fiber surface is available for removal of leucocytes, hence lower efficiency is obtained.

An objective of this invention is a leucocyte depletion device which requires no preconditioning prior to bedside use.

Wetting of Fibrous Media

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension of about 3 dynes/cm higher compared with the one preceding. A drop of each may then be placed on a porous surface and observed to determine whether it is absorbed quickly, or remains on the surface. For example, solid PTFE has a critical surface tension ($\gamma_c$) of 18 dynes/cm, and is thus by definition not wetted by a liquid with surface tension greater than 18 dynes/cm. By contrast when applying the drop technique to a 0.2 micrometer porous polytetrafluoroethylene (PTFE) filter sheet, wetting is observed for a drop of liquid with a surface tension of 26 dynes/cm, but the porous surface remains unwetted when a drop of liquid with a surface tension of 29 dynes/cm is applied. Wetting by the lower surface tension liquid is spontaneous on contact-no pressure, vacuum or other manipulation is required.

Similar behavior is observed for porous media made using other synthetic resins, with the wet-unwet values dependent principally on the surface characteristics of the material from which the porous medium is made, and secondarily, on the pore size characteristics of the porous medium. For example, fibrous polyester (specifically polybutylene terephthalate, hereinafter "PBT") sheets which have pore diameters less than about twenty micrometers will be wetted by a liquid with a surface tension of 50 dynes/cm, but will not be wetted by a liquid with a surface tension of 54 dynes/cm. This may be contrasted with the CST of solid PBT, which is about 44 dynes/cm.

In order to characterize this behavior of porous media, the term "critical wetting surface tension" (CWST) has been defined as described below. The CWST of a porous medium may be determined by individually applying to its surface a series of liquids with surface tension varying by 2 to 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's are, respectively, 27.5 and 52 dynes/cm. If the surface tension interval is an odd number, for example 3, a judgment may be made as to whether the porous medium may be closer to the lower or higher value, and on that basis, as an example, 27 or 28 might be assigned to PTFE.

In measuring CWST, a series of standard liquids for testing are prepared with surface tensions varying in a sequential manner by about 2 to about 4 dynes/cm. Ten drops each 3 to 5 mm in diameter of each of at least two of the sequential surface tension standard liquids are placed on representative portions of the porous medium and allowed to stand for 10 minutes. Observation is made after 10 to 11 minutes. Wetting is defined as absorption into or wetting of the porous medium by at least nine of the ten drops within 10 minutes. Non-wetting is defined by retention of a negative angle of contact by at least nine of the ten drops at 10 to 11 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST. When the two test fluoids differ by three dynes, a judgment is made as to how close the specimen is to one or the other, and an integral number is assigned accordingly.

Appropriate solutions with varying surface tension can be prepared in a variety of ways, however, those used in the development of the product described herein were:

| Solution or fluid | Surface Tension, dynes/cm |
|---|---|
| Sodium hydroxide in water | 94–115 |
| Calcium chloride in water | 90–94 |
| Sodium nitrate in water | 75–87 |
| Pure water | 72.4 |
| Acetic acid in water | 38–69 |
| Ethanol in water | 22–35 |

As no stable solutions with CWST >115 dynes/cm at ambient temperature were found, media with CWSt >115 were arbitrarily assigned a CWST value of 116 dynes/cm, and it should be remembered that media with this rating may have higher actual CWST values.

Wetting of Fibrous Media by Platelet Concentrate

In PC the cells are suspended in blood plasma, which has a surface tension of 73 dynes/cm. Hence, if PC is placed in contact with a porous medium, spontaneous wetting will occur if the porous medium has a CWST of 73 dynes/cm or higher.

The benefits conferred by preconditioning fibers to CWST values higher than 73 dynes/cm include:

(a) The time to achieve priming is reduced.

(b) Synthetic fiber media whose CWST values have been elevated by grafting have superior fiber to fiber bonding and are for this reason preferred for use in making the preformed elements used in this invention.

(c) A portion of the porous medium may remain unwetted. A detrimental effect associated with non-wetting is that unwetted portions are not available to remove leucocytes, in consequence of which the efficiency of removal of leucocytes by adsorption is reduced, pressure drop is increased with consequent diminution of flow, and clogging may occur.

(d) Devices made using unmodified synthetic fibers are recommended to be flushed with saline or other physiological fluid prior to use. This operation is undesirable since it causes loss of PC due to hold-up within the more complex tubing arrangement required, adds to cost, operation time, and operation complexity, and increases the probability that sterility may be lost.

DISCLOSURE OF THE INVENTION

Significant and novel features of this invention which contribute to achieving high efficiency and capacity for leucocyte removal while minimizing loss of platelets include:

(a) Whereas previously disclosed devices have used relatively small cross sectional area perpendicular to the flow path, and are correspondingly greater with respect to depth and hence to the length of their flow paths, the devices of this invention are larger in cross sectional area perpendicular to the flow path and smaller in depth, with correspondingly shorter flow path. This improvement in design contributes substantially to increased filter life, and to prevention of clogging.

(b) In order to make the larger cross sectional area economic and practical to construct, the porous components of the preferred devices in accordance with this invention are preformed prior to assembly to closely controlled dimension and pore diameter, to form an integral self-contained element.

Preforming eliminates the pressure on the inlet and outlet faces of the container which are inherent in a packed fiber system, thus making devices of large cross sectional area practical. The larger cross sectional area leucocyte depletion devices made possible by preforming have longer life in service, coupled with at least equal and usually better leucocyte removal efficiency, equal or better platelet recovery, and less hold up of fluid, when compared with devices that use fibers or fibrous webs packed into a housing at assembly.

(c) The preferred housing into which the element assembly is sealed is uniquely designed to achieve convenience of use, rapid priming, and efficient air clearance, leading to reduction of PC otherwise lost within the drip chamber.

(d) The lateral dimensions of the elements are larger than the corresponding inner dimensions of the housing into which they are assembled. For example, if the elements are of disc form, the outside diameter of the element is made about 1% larger than the housing inside diameter. This provides very effective sealing by an interference fit with no loss of effective area of the elements, and contributes further towards minimization of the blood hold-up volume of the assembly.

(e) While treating the filter surfaces to raise their CWST to 73 dynes/cm to about 90 dynes/cm is helpful with respect to accomplishing rapid wetting of the filter and to efficient passage of the platelet suspension, a filter treated to modify its surface to a CWST in the range of 73 dynes/cm to about 90 dynes/cm will adsorb a high proportion of the platelets passing through it. By modifying the filter surfaces to CWST values higher than about 90 dynes/cm, better platelet recovery is achieved. An important feature of this invention is the use of filter media with CWST values in excess of 90 dynes/cm, and preferably in excess of 95 dynes/cm. Using polyester fibrous media with fiber surfaces modified to CWST>90 to 95 dynes per cm, an increase of recovery rate together with high efficiency of leucocyte removal is obtained.

(f) The high CWST values referred to in the preceding paragraph have been accomplished by chemically attaching to the fiber surfaces a high density of hydroxyl groups. Surfaces so modified can be expected to have relatively low negative zeta potential when immersed in water in which the pH is in the normal range of a platelet suspension, i.e., about 7 to 7.2. Such surfaces absorb leucocytes efficiently, and pass a high proportion of the platelets, but are not optimal for permitting free passage of platelets.

(g) Compared with using hydroxyl modification only, a significant improvement in performance is achieved by combining with the hydroxyl groups a proportion of carboxyl groups, both chemically attached to the fiber surfaces. The observed improvement in performance may reflect the development of the fiber surfaces of increased negative zeta potential at pH 7 to 7.2. The product so modified has higher leucocyte removal efficiency coupled with very high platelet recovery.

(h) The number of carboxyl groups per unit of surface area appears to have an important effect on the adhesion of platelets to fiber surfaces. This effect is reflected in the proportion of platelets recovered in the filter effluent as a fraction of the number present in the platelets prior to filtration. As shown in FIGS. 5 and 8, platelet recovery peaks at the optimum proportion of methacrylic acid (MAA). As will be demonstrated herein the number of carboxyl groups per unit of fiber surface is, over the range of interest of this invention, close to proportional to the amount of MAA in the monomeric grafting solution.

As is evident to those skilled in the art, while adequate control to obtain product at or near the peak or FIGS. 5 and 8 can be obtained by carefully controlling all the relevant factors including monomer purity, type and quantity of inhibitor in the monomers, monomer age, precise metering of the components, use of very pure water as diluent, oxygen content of the grafting solution, the quantity of monomer solution to which each element of fibrous web is exposed, and the conditions of exposure to radiation such as radiation level and radiation time, it is highly desirable that means be available for applying a test to verify that the product indeed has the optimum surface content of carboxyl groups. This is especially the case when it is necessary to change operating mode, for example due to the use of different type or scale of apparatus, and is also very helpful in maintaining quality control during continued production. With respect to the latter, insofar as this test can be performed by a relatively unskilled person in minutes, rather than hours or days, its value is increased.

Measurement of the recovery of platelets while removing leucocytes can, of course, be used as a test. However, this is a lengthy and costly process because, for this test to provide reliable data, an average of at least about five and preferably ten tests must be performed, with each test requiring as much as a full-man day to perform, and each consuming large quantities of expensive platelets.

The discovery of the dye adsorption assay (DAA) test, which can be performed quickly while producing reliable results, is an important aspect of this invention.

As the term "leucocyte removal efficiency" will be used very frequently hereinafter, it will be shortened to "removal efficiency" or to "efficiency", and these three terms will be used interchangeably. Similarly, "Platelet recovery" and "recovery" will be used interchangeably hereinafter.

BEST MODE FOR CARRYING OUT THE INVENTION

Figure 1:
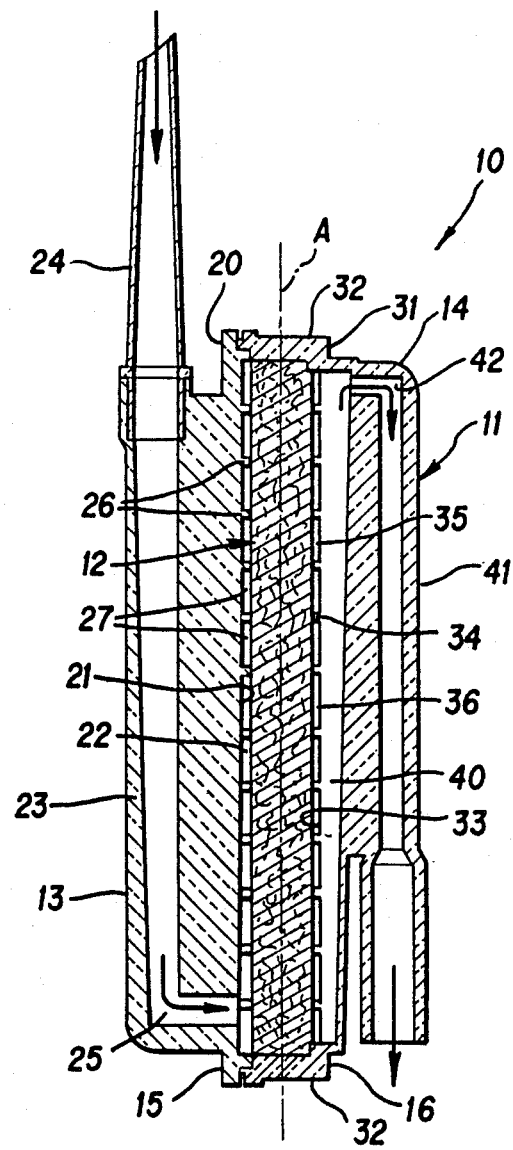
FIG. 1 is a cross sectional view of an exemplary depletion device embodying the present invention.
Figure 4:
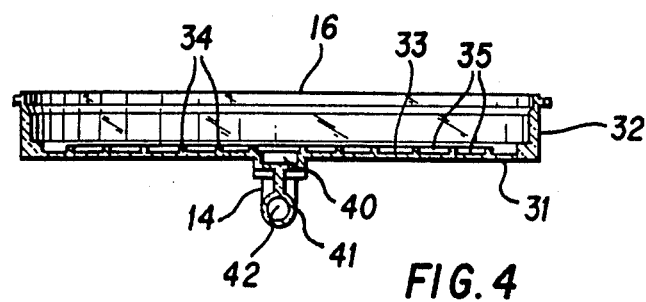
FIG. 4 is a cross sectional view of the outlet section shown in FIG. 3.

Material for Use in Construction of Devices for Removal of Leucocytes from Platelet Concentrate A variety of starting materials other than fibers can be considered; for example, porous media could be cast from resin solution to make porous membranes, or sintered powder media could be used. However, considerations of cost, convenience, flexibility, and ease of fabrication and control, point to fibers as a preferred starting material.

As discussed above, in order to achieve good priming with the fibrous medium fully wetted, blood component devices should be made of materials which have CWST values in the range of about 73 dynes/cm or higher. Practical considerations dictate a preference for the use of commercially available resins. Synthetic resins from which fibers are prepared commercially include polyvinylidene fluoride, polyethylene, polypropylene, cellulose acetate, polyamides such as Nylon 6 and 66, polyesters, acrylics, polyacrylonitriles, and polyaramids. An important characteristic of resins is their critical surface tension (Zisman, "Contact angles, wettability and adhesion", Adv. Chem. Ser. 43, 1–51, 1964). The above listed resins have critical surface tensions ($\gamma_c$) ranginng from about 27 to about 45 dynes/cm. Experience has shown that the CWST of filters in the pore size needed for the products of this invention can be expected to be less than about 10 dynes/cm higher than $\gamma_c$. For example, for 0.2 m pore diameter polytetrafluoroethylene $\gamma_c$ is 18 and CWST is 27 to 28, while for a PBT fibrous mat $\gamma_c$ is 45, and CWST is 52. Our investigation found no commercially available synthetic fiber which after formation into a web of pore size less than 20 micrometers ($\mu$m) has a CWST higher than about 52 dynes/cm.

Natural fibers smaller than about 15 $\mu$m in diameter are not generally commercially available. Synthetic webs which are less than 3 $\mu$m in fiber diameter made by the melt blowing process have been available for about 15 years, and compared with natural fibers, such fibers require one fifth or less the mass to provide equal fiber surface area for adsorption of leucocytes, and in addition occupy less volume when used to fabricate filters of a given pore size. For this reason, natural fibers are not well suited for manufacturing leucocyte removal devices with optimally low hold-up volume. For example, a commercially available packed cotton fiber device which has been tested for leucocyte depletion has a hold-up volume of over 75 ml, which is more than twice the volume of the preferred adult device described in this application. Furthermore, this device requires saline to be passed before and after the platelet concentrate has been passed, and is not suitable for bedside use, and platelet recovery is only about 50%. Additionally, blood so processed must be used within 24 hours.

The art of surface grafting has been the subject of extensive research for 25 years or more, Numerous publications in the scientific literature and a large number of patents describe a variety of methods and procedures for acomplishing surface modification by this means. One such method, which employs a variety of monomers each comprising an ethylenic or acrylic moiety together with a second group which can be selected to vary from hydrophilic (e.g., —COOH, or—OH) to hydrophobic (e.g., a methyl group or saturated chains such as —CH$_2$CH$_2$CH$_3$), has been used in the process of developing this invention. Heat, UV, and other reaction energizing methods can be used to initiate and complete the reaction. However, cobalt source radiation grafting has been selected as most convenient and has been used in this invention to modify the CWST of fibrous mats. By cut and try selection, mixtures of monomers or single monomers can be found which will produce a fibrous mat of polybutylene terephthalate in which the CWST has been increased from 52 to any desired value up to as high as is possible to be measured by the method described above. The upper limit is set by the paucity of liquids with surface tensions at room temperature higher than about 115 dynes/cm.

During the development of this invention, devices were prepared using media in which grafting was accomplished by compounds containing an ethylenically unsaturated group such as an acrylic moiety combined with a hydroxl group, for example, hydroxyethyl methacrylate (HEMA). Use of HEMA as the sole monomer produces very high CWST fibrous PBT media. Incorporation of methacrylic acid (MAA) into the monomer solution causes the zeta potential to the grafted porous medium to become more negative.

A feature of this invention is the use of the monomers specified above, or of their analogues with simmilar characteristics, to modify the surface characteristics of polyester or other organic fibers in order to influence their behavior when contacted by platelets and leucocytes suspended in blood plasma.

It has been observed that some grafting monomers or combinations of monomers, when used to treat the fibrous, porous structures as described herein, behave differently from others with respect to the span between the upper and lower values which are used to define CWST. This span can vary from less than 3 to as much as 20 or more dynes/cm. When considering media for use in the test program conducted in connection with this invention, we have preferred to use media having a span between the upper and lower values of about 5 or fewer dynes/cm. This choice reflects the greater precision with which the CWST can be controlled when narrower spans are selected, albeit media with wider spans may also be used. The use of the narrower span is preferred in order to improve product performance and quality control.

Liquids with surface tensions lower than the CWST of the porous medium will spontaneously wet the medium on contact, and if the medium has through pores, will flow through it readily. Liquids with surface tensions higher than the CWST of the porous medium will not flow at all at low differential pressures, but will do so if the pressure is raised sufficiently, If the numeric value of the surface tension of the liquid is only slightly above the numeric value of the CWST, the required pressure will be small. Conversely, if the differential is high, the pressure required to induce flow will be higher.

It has been discovered that, when a liquid is forced under pressure to pass through a fibrous mat which has a CWST lower than the liquid's surface tension, flow tends to occur in a non-uniform fashion, such that some areas of the mat remain dry. This is highly undesirable in a leucocyte depletion device, first because with only part of the porous medium permitting flow the pressure drop is higher, causing earlier clogging, second because all the flow passes through only a portion of the available area, again increasing the probability of clogging, and third because only a portion of the fiber surface area provided for adsorption of or retention by filtration of leucocytes is used for that purpose and, as a result, leucocyte removal is less efficient.

Solutions to the Problem of Poor Wetting of Synthetic Fibers

Fiber surface characteristics can be modified by a number of methods, for example, by chemical reaction including wet or dry oxidation, by coating the surface or depositing a polymer thereon, and by grafting reactions which are activated by exposure to an energy source such as heat, a Van der Graff generator, ultraviolet light, or to various other forms of radiation, among which $\gamma$-radiation is particularly useful.

As an example of these various methods, synthetic organic fibers may be coated by polymers which contain at or near to one end a reactive (e.g., epoxide) moiety and at the other a hydrophilic group.

While the above methods and others known to those familiar with surface modification art can be used, radiation grafting, when carried out under appropriate conditions, has the advantage that considerable flexibility is available in the kinds of surfaces that can be modified, in the wide range of reactants available for modification, and in the systems available for activating the required reaction. In the subject invention $\gamma$-radiation grafting has been focused on because of the ability to prepare synthetic organic fibrous media with CWST over the full range of interest, which is from about 73 to 85 to above about 115 dynes/cm. The products are very stable, have undetectably low aqueous extractables levels and, in addition, have improved adhesion between fibers when used in preformed elements.

Selection of Fiber Diameter for Use in Leucocyte Depletion Devices

Adsorption of leucocytes on fiber surfaces is generally accepted as the mechanism of leucocyte removal. Since the surface area of a given weight of fibers is inversely proportional to the diameter of the fibers, it is to be expected that finer fibers will have higher capacity and that the quantity as measured by weight of fibers necessary to achieve a desired efficiency will be less if the fibers used are smaller in diameter.

For this reason, the trend has been to use finer fibers for leucocyte depletion. Historically, as the technology required to produce smaller diameter fibrous webs has advanced, they have soon thereafter been packed into housings and used for leucocyte depletion, as well as for a wide variety of other purposes, such as industrial filtration. The performance of all of these previously made devices is inferior to that of the products in accordance with this invention.

Selection of Fiber for Leucocyte Depletion Devices

A number of commonly used fibers, including polyesters, polyamides, and acrylics, lend themselves to radiation grafting, as they have adequate resistance to degradation by $\gamma$-radiation at the levels required for grafting and are of a structure with which available monomers can react.

As noted above, fiber diameters should be as small as possible. Synthetic fibers made by conventional spinneret extrusion and drawing are not currently available smaller than about 6 micrometers in diameter.

Melt blowing, in which molten polymer is attenuated into fibers by a high velocity stream of gas and collected as a non-woven web was first disclosed in the 1950's and reported to make fibers as small as one micrometer in diameter, came into production in the 1960's and 1970's and has been gradually extended over the years with respect to the lower limit of fiber diameter with which coherent webs could be made. Within recent years, webs with fiber diameters as small as about 1.5 to about 2 micrometers have been achieved. Even smaller diameter fibers can be made, but these are difficult to collect as continuous web.

Some resins are better adapted to melt blowing of fine fibers than are others. Resins which work well include polyethylene, polypropylene, polymethylpentene, Nylon 6, polyester PET (polyethylene terephthalate), and PBT (polybutylene terephthalate). Of the above listed resins, PBT is a preferred material because it also lends itself to radiation grafting and to subsequent conversion into preformed elements of controlled pore size by hot compression.

PBT has been the principal resin used for the development of the products of this invention and is the resin used in the examples. It should be noted, however, that other resins may be found which can be fiberized and collected as mats or webs with fibers as small as 1.5 micrometers or less, and that such products, with their CWST adjusted as necessary to the optimum range, may be well suited to the fabrication of equally efficient but still smaller leucocyte depletion devices. Similarly, glass fibers, appropriately treated, may be usable to make effective devices. Devices made using these or other fibers in the manner and for the purposes described in this invention should be understood to be within the scope of this invention.

Description of an Exemplary Depletion Device

As shown in FIGS. 1-4, an exemplary depletion device 10 generally comprises a housing 11 and a filter-adsorber 12. The housing 11 has an inlet 13 and an outlet 14 and defines a fluid flowpath between the inlet 13 and the outlet 14. The filter-adsorber 12 is disposed within the housing 11 across the fluid flowpath and serves to separate undesirable substances, such as red cells, gels, fat globules, aggregates, and leucocytes, from a fluid, such as a suspension of platelets in blood plasma, flowing through the housing 11.

Housings can be designed to accept a variety of shapes of filter-adsorber assemblies. One such is, for example, a square. Those and other possible forms would in principle all be functional, provided that adequate flow area is provided.

A square filter-adsorber assembly would in theory allow more economical use of material, but would be less reliable if an interference fit seal is used in the manner described below for housings fitted with disc shaped filter-adsorber assemblies. If sealing is obtained by edge compression about the periphery, significant effective area is lost at the seal. For those reasons, cylindrical housings with disc shaped filter-adsorber assemblies assembled with an interference fit seal are preferred, although other forms may be used. The seal obtained by edge compression may be supplemented by a compression seal, in which case the compression seal can be very narrow or provide minimal compression, with very small loss of effective area.

Housings can be fabricated from any suitably impervious material, including an impervious thermoplastic material. For example, the housing may preferably be fabricated from a transparent polymer, such as an acrylic, polystyrene, or polycarbonate resin, by injection molding. Not only is such a housing easily and economically fabricated, but if transparent it also allows observation of the passage of the fluid through the housing. The housings are designed to withstand normal abuse during service, as well as internal pressures up to about 3 psi (0.2 Kg/cm²). This permits light construction, which is a desirable feature of this invention made possible by the use of preformed filter-adsorber assemblies. The force required to compress the fibers of an efficiently designed filter-adsorber assembly in which the element has not been preformed but instead is made by packing of fibers into a housing, can be as high as about 70 kilograms for a 62 cm² disc, of about 1.1 kg/cm², requiring heavier, bulkier, and more costly housing construction.

While the housing may be fashioned in a variety of configurations, the housing 11 of the exemplary separation device 10 is preferably fashioned in two sections, i.e., an inlet section 15 and an outlet section 16. The inlet section 15 includes a circular inlet plate 20, and the inside surface of the circular inlet plate 20 defines a wall 21 which faces but is not in contact with the upstream surface of the filter-adsorber element 12.

Figure 2:
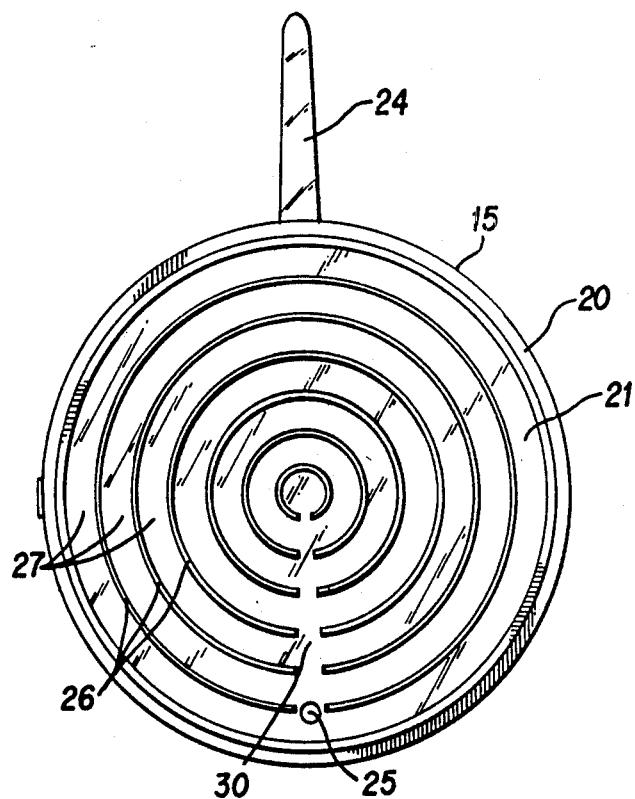
FIG. 2 is an elevation view of the inside surface of the inlet section of the depletion device shown in FIG. 1.
Figure 3:
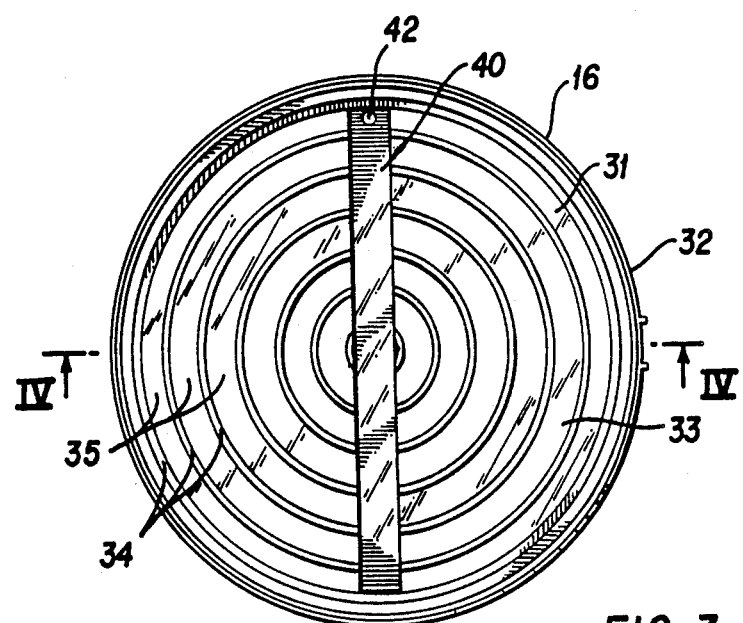
FIG. 3 is an elevation view of the inside surface of the outlet section of the depletion device shown in FIG. 1.

The inlet 13 delivers the fluid to an inlet plenum 22 between the wall 21 and the upstream surface of the filter-adsorber element 12. In accordance with one aspect of the invention, the inlet 13 delivers the fluid to the inlet plenum 22 at or near the bottom of the housing 11, as shown in FIGS. 1 and 2.

The inlet may be variously configured. However, the inlet 13 of the exemplary separation device 10 includes a longitudinal inlet ridge 23. The inlet ridge 23 extends along the outside surface of the circular inlet plate 20 parallel to a diametrical axis A of the housing 11, which, in use, is positioned with the diametrical axis A oriented generally vertically. The upper end of the inlet ridge 23 may be fashioned as a socket for receiving a hollow spike 24 which is used to pierce the bottom of a bag containing the fluid, e.g., a platelet concentrate bag. The inlet 13 further includes an inlet passageway 25 which opens at the upper end of the hollow spike 24, extends through the hollow spike 24 and the inlet ridge 23, and communicates with the inlet plenum 22 at the bottom of the inlet section 15.

The wall 21 of the circular inlet plate 20 includes a plurality of generally concentric circular ridges 26 which define concentric circular grooves 27. The ridges 26 abut the upstream surface of the filter-adsorber assembly 12. As shown in FIG. 2, the ridges 26 terminate in the lower portion of the inlet section 15, defining a passageway or access 30. The access 30 extends between the inlet passageway 25 and each circular groove 27, allowing fluid to flow from the inlet passageway 25 to the circular grooves 27. Collectively, the circular grooves 27 and the access 30 define the inlet plenum 22, which distributes the fluid delivered by the inlet passageway 25 over the whole upstream surface of the filter-adsorber element 12. To prevent aggregates and other large obstructions from blocking flow at or near the junction of the inlet passageway 25 and the inlet plenum 22 and, at the same time, to minimize hold-up volume in the housing 11, the depth of the inlet plenum 22 is greatest at the bottom of the housing 11 and decreases along the vertical axis A to a minimum value at the horizontal centerline of the housing 11.

The outlet section 16 of the housing 11 includes a circular outlet plate 31 and a cylindrical collar 32 which extends from the periphery of the circular outlet plate 31 to the periphery of the circular inlet plate 20. The cylindrical collar 32 is preferably integrally formed with the circular outlet plate 31 and joined to the circular inlet plate 20 in any suitable manner, e.g., by an adhesive or by sonic welding.

The inside surface of the circular outlet plate 31 defines a wall 33 which faces but does not contact the downstream surface of the filter-adsorber element 12. The wall 33 includes a plurality of generally concentric circular ridges 34 which define concentric circular grooves 35. The ridges 34 abut the downstream surface of the filter-adsorber element 12. The circular grooves 35 collectively define an outlet plenum 36 which collects the fluid passing through the filter-adsorber element 12. The depth of the outlet plenum 36 is made as small as possible to minimize hold-up volume within the housing 11 without unduly restricting fluid flow.

In accordance with another aspect of the invention, the wall 33 further includes a passageway such as a slot 40 which communicates with the outlet 14 at or near the top of the outlet section 16. The slot 40, which collects fluid from each of the circular grooves 35 and channels the fluid to the outlet 14, preferably extends from the lower portion to the top of the outlet section 16 parallel to the vertical axis A. In one configuration of the exemplary separation device 10, the width of the slot 40 remains constant but the depth of the slot 40, which is greater than the depth of the outlet plenum 36, increases from the lower portion to the top of the outlet section 16 along the vertical axis A. The length of slot 40 may be equal to or less than the diameter of the housing, and the width may vary while the depth may remain constant, or both the width and depth may vary.

The outlet 14 may be variously configured. However, the outlet 14 of the exemplary depletion device 10 includes a longitudinal outlet ridge 41 which extends along the outside surface of the outlet plate 31 parallel to the vertical axis A. The lower end of the outlet ridge 41 may be fashioned as a tubing connector or as a socket for receiving a tubing connector or other apparatus. The outlet 14 further includes an outlet passageway 42 which communicates with the slot 40 at or near the top of the housing 11, extends through the outlet ridge 41, and opens at the lower end of the outlet ridge 41.

As platelet concentrate starts to flow through the apparatus, filling it from the bottom and emptying at the top, air is displaced and flows towards and out of outlet passageway 42. By careful design of the exemplary apparatus it has been possible to reduce and very nearly eliminate completely, the situation in which some liquid reaches the area 43 adjacent to the outlet passageway 42 before all of the air is cleared form the inner parts of the housing assembly. In the absence of slot 40, this lagging air flow would carry some platelet suspension into the outlet tube 42. Slot 40 allows the platelet suspension so carried to flow into the slot, where the air is harmlessly separated from the liquid suspension. The air then rises harmlessly to the outlet 14 ahead of the rising fluid level in the slot 40 and is completely or almost completely ejected before the liquid level reaches the top of the outlet plenum 36 and outlet passageway 42. Thus, air is very efficiently cleared from the housing 11 of the exemplary depletion device 10 according to the invention. For example, in a depletion device which has an inside diameter of 89 millimeters, an initial air volume of 20 cc, and a 5 centimeter long slot which is 0.3 centimeters wide and 0.2 centimeters deep at the bottom, and 0.3 centimeters deep at the top, the residual volume of air passing through the outlet after 1 to 2 cc of liquid has passed through the outlet is estimated to be less than 0.1 cc.

In order to understand the importance of the slot and the flow passage configuration, the equivalent operation of a conventional leucocyte depletion unit will be described.

In conventional units, fluid enters at the top of the housing and exits at the bottom. The housing of such a unit cannot be directly connected by a spike integral with the housing, and instead is typically connected by plastic tubing to a spike which is used to penetrate a bag upstream from the conventional housing. A transparent drip chamber is connected by tubing downstream from both the conventional and novel housings, and thence to the patient. During priming, the conventional housing along with the drip chamber are inverted and liquid is forced through the conventional housing into the drip chamber. This has the disadvantage that some pressure head is lost, but, more seriously, fluid reaches the exit of the conventional housing and enters the drip chamber while as much as 1 to 2 cc or more of air is still trapped in the conventional housing. When 3 or 4 cc of fluid has been collected in the drip chamber, it and the housing are returned to their normal position, leaving a reservoir of 3 to 4 cc of fluid in the bottom of the drip chamber. With the novel housing of this invention, only the drip chamber is inverted during priming, and only about one cc of fluid is collected in the drip chamber before returning it to its normal position.

The transparent drip chamber performs a service in permitting observation of the droplet rate through the air space, thus providing guidance for flow regulation. It also performs a second service in that lagging air entering from the conventional housing is prevented from reaching the patient. This is so because the lagging air displaces an equivalent volume of fluid in the reservoir of the drip chamber. However, the reservoir must be large enough to ensure that the lagging air never totally displaces the fluid; otherwise, air may enter the vein of the patient.

Systems which permit a significant volume of air, e.g., 2 to 3 cc, to reach the drip chamber after it has been returned to its normal position, tend to do so non-reproducibly. Thus, the larger the volume of lagging air, the larger the volume of fluid which must be collected during priming in the reservoir of the drip chamber. At the end of the administration, much of that volume is left in the drip chamber and, hence, is wasted. By maximizing air clearance and thereby allowing the use of a smaller reservoir in the drip chamber, the depletion device according to the present invention significantly reduces the amount of always costly and sometimes difficult to obtain PC wasted during administration.

The filter-adsorber element 12 preferably comprises a single preformed layer as described below under the heading Fabrication of Fibrous Elements. During the development stage, housings were constructed for use in testing, which incorporated the basic internal configuration described above, but in addition were variable with respect to the thickness of the filter-adsorber element. In this way, it was possible to test filter-adsorber elements varying in total thickness. In each case, the distance between the tips of the ridges 26, 34 of the inlet and outlet sections was adjusted to be equal to the nominal total thickness of the preformed element.

To provide an interference fit of the filter-adsorber element 12 within the housing 11, the filter-adsorber elements were cut from the precompressed slab to a diameter up to about 1% larger than the inside diameter of the cylindrical collar 32. The filter-adsorber elements were cut in such a manner as to maintain true right cylindrical form at their outer edges. This, coupled with the slight oversizing, surprisingly provides good edge sealing, by means of an interference fit between the outer edges of the preformed element 12 and the inner periphery of the housing 11, with 100% utilization of the full area and volume of the filter-adsorber assembly 12, thereby minimizing hold-up volume.

Fabrication of Fibrous Elements in the Preferred Form

The preferred upper limit of average fiber diameter is about 6 $\mu$m, however, filters with larger fiber diameters, for example up to about 10 to 15 $\mu$m which have useful efficiency and recovery can be made, but such filters have increased loss of PC due to retention within the correspondingly larger filter elements of PC which is not delivered to the patient, hence are less desirable. The lower limit of fiber diameter at this time is the lower limit of average fiber diameter with which fibrous webs which are readily modifiable to CWST values in excess of about 85 dynes/cm can be made, about 1.5 to 2 $\mu$m. Should finer fibers become available in the future, they may perform similarly or better than those used to make the products of this invention.

For use in the products of this invention, melt blowing means are preferred which produce webs in which the fiber diameter size distribution is as narrow as possible.

The web is treated to modify the fiber surfaces, either before or after forming the fibrous lay-up. It is preferred to modify the fiber surfaces before forming the fibrous lay-up because a more cohesive, stronger product is obtained after hot compression to form an integral filter element.

The method used for modifying the fiber surfaces while developing the products of this invention is $\gamma$-radiation grafting, however, other methods known to those familiar with the art may be used to increase the CWST of the web.

The grafting procedure is directed towards producing web with the highest possible CWST. The CWST preferably exceeds about 90 dynes/cm, and more preferably exceeds about 93 dynes/cm.

Monomers terminating with hydroxyl or carboxyl or other neutral or electronegative end groups are preferred. Inclusion of or use of monomers with hydrophobic or electropositive groups tends to cause adhesion and consequently low recovery of platelets.

Surface modification has been performed on the fibrous medium in the form of web as made by the melt blowing process, usually in roll form; in the form of slabs made by compressing single or multiple layers of the web to the desired density; and in the form of discs cut from the slabs. To accomplish fiber surface modification these alternate forms are immersed in an aqueous solution containing about 0.05 to 1% by weight of a monomer of molecular composition comprising an unsaturated reactive moiety at or near one end of the molecule, for example, an acrylic group, and one or more non-reactive hydroxyl groups at the other end of the molecule. Unbranched linear compounds have been preferred, such as, for example HEMA (hydroxyethylmethacrylate); other monomers which may be used include hydroxypropylacrylate, hydroxyethylacrylate, and hydroxypropylmethacrylate. These are commercially available as the Rocryl TM 400 series from Rohm and Haas. These four are examples, but more generally any hydroxyalkylacrylate or hydroxyalkylmethacrylate, and a variety of related monomers may be suitable. The solution may include a second water soluble compound capable of reducing the surface tension of the grafting solution so as to better wet the fibers, for example, about 2 to 10%, and preferably about 4 to 5% by weight, of tertiary butyl alcohol (t-BuOH), or roughly similar percentages of diethylene glycol monobutyl ether or of ethylene glycol monobutyl ether. An optional third component, which is preferred to be used because it provides a significant improvement in platelet recovery while maintaining a high efficiency of leucocyte removal, is 0.01 to 0.2% or more of a monomer in which the non-reactive end of the molecule contains one or more carboxyl groups, for example, acrylic acid or methacrylic acid (MAA). Other suitable monomers include unsaturated mono, or di-carboxylic acids, for example itaconic acid, or anhydrides such as maleic anhydride. In general, all that is necessary is an ethylenically unsaturated bond along with a group having anionic character such as a carboxyl or sulfonic acid group.

While $\gamma$-irradiation by cobalt has been used in the development of this invention, other forms of radiation or other types of energy source may be used. The time of exposure at a given radiation or energy level is best determined by trial and error. During the development of this invention, total exposures in the range of about 0.01 to 1.5 megarads over periods of about 6 to 60 hours have been used.

After removal from the spent grafting solution the web, slab, or precut shape is water washed to remove spent grafting solution, then dried at any convenient temperature up to about 175° to 225° C. The dried product may after cooling be tested by applying over a representative area drops of a test fluid of surface tension of preferably at least about 90 dynes/cm, and more preferably 93 dynes/cm. Spontaneous wetting by or absorption of drops of surface tension greater than about 90 dynes/cm within a 10 minute period indicates adequately high CWST.

A second test may be applied, the purpose of which is to verify that the content of carboxyl or carboxylic or other acid groups is optimal for achieving the highest or near to the highest possible recovery of platelets. In this test, a column of the dried filter medium is prepared, preferably with a height of about 0.7 cm, and a solution of a dye substantive to anionic surfaces is passed through the column. The dye is initially completely adsorbed from solution by the column, such that the issuing liquid is colorless. Passage of the dye solution is stopped when color first appears downstream of the filter medium. The volume of dye solution passed is proportional to the acid group content of the surface of the grafted fibers.

One or more layers of dried web are heated to about 175° to 325° C. and compressed, for example between hot platens, to form a self supporting "slab" of the required density, thickness, and pore diameter.

After cutting to size from the slab to the form of a right cylinder, a self contained preformed filter element is obtained, which is then inserted into the housing described above and the two parts of the housing sealed, providing a finished filter assembly ready to be connected at its inlet end to a device for piercing a bag of platelets, and at its outlet end to a drip chamber and a catheter, which after sterilization and packaging constitutes an administration set suitable for bedside infusion of leucocyte depleted platelet concentrate to a patient.

As will be demonstrated in the examples, the effective flow area, which is defined as the area through which the platelet suspension flows, is preferred to be in excess of about 40 cm$^2$, while an area in excess of 50 cm$^2$ is more preferred, and an area in excess of 60 cm$^2$ is still more preferred.

When used with platelets aged three to five days or more, filters with effective flow area much less than about 50 to 60 cm$^2$ are prone to excessive frequency of clogging prior to passage of the full volume of 6 to 10 units of platelet concentrate. If for some reason an element with effective flow area less than about 60 cm$^2$ is preferred, this may be made using a correspondingly thicker preform as the filtering element, and the frequency of clogging can be minimized by providing prefiltration layers; however, doing so increases hold-up volume and increases complexity of manufacture, and for these reasons the use of a filter with an effective flow area of less than 50 or 60 cm$^2$ is less preferred. Relatively smaller flow area can also be used with reduced likelihood of clogging by utilizing filter media of very low density, for example less than 0.05 to 0.1 g/cc; however, the losses of PC by retention within the filter element using this alternate are excessively large.

The total surface area of the fiber incorporated into a filter assembly must be matched to the quantity of platelets to be processed. For a typical platelet concentrate containing 10$^9$ platelets per cc, the fiber surface area required is about 0.007M$^2$/cc. for example, if the average volume per unit of platelet is taken to be 55 ml, and a pool of 8 units are to be processed, the required fiber surface area is:

$$55 \times 8 \times 0.007 = 3.1 M^2$$

With this area, on average, leucocyte content will be reduced by about 99.0 to 99.9%, and platelet recovery in the filtrate will be about 85 to 95%. If more than about 0.009M$^2$ of fiber surface per cc is used, efficiency will increase towards 100%, while recovery will fall. If less is used, efficiency is reduced while recovery increases. Fiber surface areas in the range from about 0.005 to 0.02M$^2$ per cc of platelets are useful. The lower part of this range is preferred if the primary objective is to achieve a high recovery of platelets (e.g. 95 to 99%) while accepting low leucocyte removal efficiency (e.g. 90 to 99%). The higher part of the range is useful if the objective to achieve very high leucocyte removal efficiency (e.g. over 99.9%) while accepting low (e.g. as low as 50% or less) platelet recovery.

Common U.S. hospital practice is to use 6 to 10 units of platelets for transfusion of adults while neonates receive as little as one half of a unit. While the adult range can be served reasonably well by a filter designed for use with 8 units, pediatric transfusions must use filters with proportionally smaller fiber surface areas.

Characterization of Porous Media by Physical Characteristics

Various formulae have been proposed for use in calculating the pore diameter of a fibrous filter from the fiber diameter, the density of the fiber, and the bulk (apparent) density of the filter medium. None of these have proven to be useful, as they fail to take into account pore size distribution, and the effect of altering the thickness of the filter medium is not adequately predicted by such formulae. Most importantly, the particle retention capabilities are not correctly predicted by such formulae.

One such formula, for example, purports to calculate the average distance between fibers. However, the average distance between fibers can not be a meaningful predictor of performance, as in any liquid flow path it is the largest pore or pores encountered which control performance. In a fibrous mat such as made by melt blowing, the fibers are laid down in a random manner, and the pore size distribution is quite wide. Other means for forming fibrous mats, e.g., air laying, or formation on a Fourdrinier screen, also produce wide pore size distributions. If two filters both have equal average fiber separation, hence equal average pore diameter, but one is relatively wider with respect to pore size distribution, then that one will pass particles which are larger. Thus the average distance between fibers is a poor predictor of performance when filtering hard particles, and the behavior of deformable "particles" such as leucocytes and platelets is even less predictable. This formula can not, in particular, be predictive of the products of this invention, which are made by the melt blowing process. In this process, the fibers issue from spinnerets in which molten resin is attenuated to fibrous form by a stream of air, whence they impinge on and adhere to a moving substrate (which is subsequently discarded). The fibers are not randomly distributed, rather they tend to be aligned parallel to the direction in which the disposable substrate is moving. A formula which fails to factor in the degree to which the fibers are parallel can not yield meaningful results. Further, the so formed web is subsequently compressed during hot preforming. During compression, the density is increased, and the average fiber—fiber spacing is decreased perpendicular to the plane of the sheet, but remains unchanged in the direction parallel to the plane of the sheet. A variety of other formulae have been proposed to allow calculation of pore diameters from data on fiber diameter, fiber density and bulk density, but in over forty years of devising means to make and apply filter media, the more senior of the inventors of the subject invention has never found any formula useful for calculating a priori the effective pore diameter of filters for removal of solids from liquid suspension.

Mathematical modelling of a system to remove leucocytes while passing platelets freely is even less likely to be successful because both leucocytes and platelets are physiologically active. When contacted by a variety of surfaces, many or all of these cells can emit a variety of enzymes, growth factors, and other active agents, and further they can change shape and may become motile, in manners and for reasons currently only partially at best understood.

Further, leucocyte removal from PC is accomplished by adsorption, rather than filtration. As is demonstrated below, leucocyte removal is dependent on pore diameter to a minor degree, if at all, and the utility of measuring pore diameter is essentially confined only to determining the minimum diameter range at which recovery is not adversely affected, as will be seen in the examples below.

Under these circumstances, it was necessary in the development of this invention to use cut and try methods. These were based in part on knowledge and in part on intuition, but in large part the development efforts which resulted in this invention were empirical.

Measurement of fiber surface area, for example by gas adsorption—popularly referred to as "BET" measurement—is a useful technique, as the surface area is a direct measure of the extent of fiber surface available to remove leucocytes by adsorption. In addition, the surface area of melt blown PBT webs can be used to calculate average fiber diameter as follows:

$$\text{Total volume of fiber in 1 gram} = \frac{1}{1.38} \text{ cc} \quad (1)$$

(where 1.38 = fiber density of PBT, g/cc)

$$\text{hence } \frac{\pi d^2 L}{4} = \frac{1}{1.38}$$

Fiber surface area is $\pi d L = A_f$ \quad (2)

Dividing (1) by (2), $\frac{d}{4} = \frac{1}{1.38 A_f}$ and $d = \frac{4}{1.38 A_f} = \frac{2.9}{A_f}$, or $(0.345 A_f)^{-1}$ where L=total length of fiber per gram, d=average fiber diameter in centimeters, and $A_f$=fiber surface area in cm$^2$/g.

If the units of d are micrometers, the units of $A_f$ become M$^2$/g, which will be used hereinafter.

Average fiber diameter is defined above in terms of $A_f$; however, when comparing two of the performed fibrous elements of this invention, one of which has a significantly narrower fiber diameter range than the other, the element with the narrower distribution will perform better as a leucocyte removal filter. For this reason, elements are preferred to have as narrow as possible a distribution of fiber diameters.

Another characteristic necessary to describe a porous medium adequately to permit it to be reproduced is its pore diameter (Dp). Pore diameters of filter media were determined using the modified OSU F2 method and are reported as the diameter of hard particle at which 99.9% of the incident particles were removed. The F2 test used in making pore size measurements is a modified version of the F2 test developed in the 1970's at Oklahoma State University (OSU). In the OSU test, a suspension of an artificial contaminant in an appropriate test fluid is passed through the test filter while continuously sampling the fluid upstream and downstream of the filter under test. The samples are analyzed by automatic particle counters for their contents of five or more preselected particle diameters and the ratio of the upstream to downstream count is automatically recorded. This ratio is known in the filter industry as the beta ratio.

The beta ratio for each of the five or more diameters tested is plotted as the ordinate against particle diameter as the abscissa, usually on a graph in which the ordinate is a logarithmic scale and the abscissa is a log$^2$ scale. A smooth curve is then drawn between the points. The beta ratio for any diameter within the range tested can then be read from this curve. Efficiency at a particular particle diameter is calculated from the beta ratio by the formula:

$$\text{Efficiency, percent} = 100\left(1 - \frac{1}{\text{beta}}\right)$$

As an example, if beta=100, efficiency=99%.

Unless otherwise stated, the pore diameter Dp cited in the examples presented herein is the particle diameter at which beta=1,000, hence, the F2 efficiency at the pore diameters cited is 99.9%.

In the modified F2 test, efficiencies in the pore diameter range of from 1 to 20–25 micrometers were determined using as a test contaminant an aqueous suspension of AC fine test dust, a natural silicious dust supplied by the AC Spark Plug Company. Prior to use, a suspension of the dust in water was mixed until the dispersion was stable. Test flow rate was 44 liters per minute per square foot of filter area.

The F2 test yields an absolute value of the pore diameter, but requires several hours for each test to be run. In order to reduce the time required, data obtained by the F2 test were correlated with a quantified version of the "bubble point test" which is called the "forward flow test", both of which are known to those familiar with the development and use of filters, and the correlation was used to interpolate the F2 data, thus reducing the number of F2 tests required.

Characteristics in addition to Dp which describe a porous medium include apparent or bulk density ($\rho$) in grams/cubic centimeter (g/cc), the fiber density (also in g/cc), the thickness (t) of the medium, specified in centimeters (cm), the effective flow area of the filter element ($A_c$) in square centimeters (cm$^2$), the surface area of the fibers ($A_f$) in M$^2$/g, the fiber diameter distribution, and the CWST in dynes/cm.

Specifying these parameters defines a filter or filter-adsorber element of predictable behavior when used for leucocyte depletion:

(a) $A_f$, the fiber surface area per gram, when multiplied by the effective flow area, filter element thickness and density ($A_f \times A_c \times t \times \rho$) of the filter, is the fiber surface area (FSA) available within the filter element for removal of leucocytes by adsorption. Further, relatively uniform fiber diameter distribution is preferred.

(b) An objective of this invention is a filter which will pass a pool of ten units of PC as much as 3 to 5 days old without clogging. Insofar as $A_c$ exceeds about 50 to 60 cm$^2$, clogging with 10 units of 5 day old PC will be infrequent, and clogging with fresher PC will be very rare, or will not occur at all.

(c) Dp optimally is adjusted to be just large enough that platelets are not removed by filtration. The data obtained in the course of the development of this invention show that once this condition has been satisfied, Dp can be increased further by a factor of about two to four with no effect on leucocyte removal efficiency, but with increased PC loss due to increased hold up of PC within the filter.

A fibrous filter-adsorber element for leucocyte depletion of PC is defined by specifying the density and fiber diameter distribution of the fibers from which it is made, as well as $A_c$, $A_f$, Dp, $\rho$, t, its CWST, and by conforming to the rules for monomer selection described herein.

BET surface areas were measured after the fiber surfaces had been altered by grafting, but before hot compression to form a slab of the medium from which the preformed elements of this invention were cut.

EXAMPLES

The platelet concentrate (PC) used in these examples was obtained from donated human blood anticoagulant treated with CPDA-1, using procedures which conform to American Association of Blood Banks standards. The source of supply was the Greater N.Y. Blood Program in Melville, N.Y.

It is current transfusion practice in the United States to pool 6, 8 or 10 units of PC, where a unit of PC is defined as the quantity obtained from a single usually 400 to 500 ml blood donation. Four sizes of filter housings with effective flow areas ($A_c$) of 4.47, 17.8, 31.7, and 62.1 cm$^2$, were used in the examples which follow. These sizes are referred to hereinafter respectively as sizes A, B, C and D. Size D is preferred for use in transfusion of adults.

Filters equal in all respects other than $A_c$ will have capacity for leucocyte removal proportional to $A_c$, provided that the test flow rates used are proportional to $A_c$, hence the behavior of any one of these sizes can be calculated from tests run using any other size. In order to make comparison of the data reported in the examples convenient, we have unless noted reported herein the values obtained using the D size element, or those obtained by using a smaller size and then calculating the results which would be obtained with the D size.

In presenting the results of the examples, the term "efficiency" expressed in percent is used to denote 100 multiplied by the ratio $$\frac{C1 - C2}{C1},$$

where C1 is the leucocyte content per unit volume in the PC, and C2 is the leucocyte content per unit volume in the effluent. The term "recovery" is used to denote the efficiency of platelet recovery, expressed in percent and is 100 times the ratio of the average concentration of platelets in the effluent to the concentration of platelets in the influent PC. Since the devices of this invention are designed to be used principally with 6 to 10 units of platelets, the data for the efficiency and recovery for 6, 8 and 10 units are listed separately, and the average of the 6, 8 and 10 units data is also listed. This last number is a useful guide to the average performance which may be expected in hospital service.

The test flow rate was controlled to 7 cc/minute for a size D device, which is our estimate of the average of normal hospital bedside practice, and "clogging" as used herein is defined as the condition in which the flow through a size D device falls below 1.75 cc/minute at a pressure head of 102 cm of water column.

The test flow rate of 7 cc/minute for the size D device, or its equivalent for A, B and C size was unless otherwise noted maintained during each test by adjusting the pressure head between the bag and the location of the tube end from which the leucocyte depleted PC was collected. If the pressure head reached 102 cms, it was subsequently held at that level until flow fell to 1.75 cc/minute, and at that point the test was terminated, and the filter was considered to have clogged. If the final flow rate exceeded 1.75 cc/minute or its equivalent for the A, B or C size filters, all of the PC had been withdrawn from the pooled bag, and the filter had not clogged.

Test runs using the A size filters were run four in tandem, using a single bag of six pooled PC units. The flow from the bag was divided into four equal parts, each delivered to an A size filter.

All leucocyte counts were made by conventional chamber counts, by well-trained technicians, and data reported is the average of at least two counts by different technicians. For most of the examples dilution of the filtered effluent for counting was such that 1 count=55 leucocytes. Towards the end of development, when most effluents showed zero leucocytes, the count ratio was made twenty-five times more sensitive by using a dilution ratio of 1 to 2.2. Data reported to two decimal places were obtained using the 1 to 2.2 dilution ratio.

Use of an automatic counter for determining the leucocyte content of the effluent from an efficient filter provides incorrect results, because automatic counters are designed to be operated in the range of normal leucocyte content of normal PC. Thus, the normal operating range of automatic counters is about 100 to 10,000 times higher than the levels reached in the examples herein; as a consequence, at the low levels contained in the filter effluent, automatic counter data are not reliable. Put otherwise, leucocyte counts obtained for the effluent of an effective leuocycyte depletion device are below the noise-to-signal ratio of automatic counters. Counts must therefore be done manually. Platelet counts for PC as received from the blood bank were obtained using a Coulter Counter Model No. ZM.

The elements used in the examples were of disc form. For the D size element, diameter as made was 89.1 to 89.8 mm, compressed to 88.9 mm diameter at assembly. Similarly C size elements were 63.7 to 64.1 mm discs compressed to 63.5 mm at assembly, and the corresponding numbers for B size are 47.8 to 48.1 and 47.6 mm, and for the A size 24.0 to 24.1 and 23.9 mm.

An element with a total thickness of t was assembled into a housing of internal configuration as described above, with a clearance of t between the faces of the two plenums, i.e., between the tips of the ridges 26 on the inlet plate 20 and the tips of the ridges 34 on the outlet plate 31, as shown in FIG. 1.

The definition of a unit of PC, as used herein is the quantity of PC obtained from a single 400 to 500 ml blood donation. The volume of a unit is recommended by the AABB (American Association of Blood Banks) to be 50 to 70 ml, but smaller units, down to as low as 40 ml are occasionally obtained. We have estimated and used 55 ml to be the average volume of a PC unit. In order to put all of the data on the same base, so that comparisons of data obtained using the different sizes of elements can be readily made, the flow volume data for the A, B and C sizes are calculated to the D size equivalents for passing 6, 8 or 10 units of volume 55 ml per unit.

During the research which resulted in this invention, it was conceived that better results might be obtained if melt blown web with a narrower range of fiber diameter could be made, and this was thereafter successfully accomplished. The fiber diameter distribution used in the earlier examples (1–93 and 163) of this invention were seen on inspection of scanning electron micrographs (SEM's) to be wider in range when compared with SEM's of examples 94–162. As may be seen below, the narrower size distribution is preferable.

Examples 1–121 and 163 were grafted using a monomer containing 0.43% HEMA, 0.082% MAA, and 4.7% of t-BuOH by weight in water. In the remaining examples, 122–162, the composition of the grafting solution was varied as noted for each category of test.

All of the elements used in the examples were preformed to slabs of controlled thickness and density, and right circular discs were then cut from the slabs, forming a test element.

Example numbers 1–24 are presented in Table 1. As previously noted, it is U.S. practice to use platelets no older than five days. Because PC develop gels and aggregates even when stored under optimal conditions, the older the PC the more likely it is to cause filter clogging. Hence, determination of adequacy to pass one PC unit without clogging is best accomplished using relatively old PC.

The data of Table 1 was obtained using PC of the ages noted, with elements made using 6 m diameter fibers with CWST values in excess of 96 dynes/cm$^2$ and with the optimal content of acid monomer, compressed to a density of 0.42 grams/cc.

This group of examples demonstrates capability to deliver a full 8 to 10 units in a majority of the tests even with PC beyond its expiration date. Examining the performance with 5 day old PC as shown by examples 9–24, three of the sixteen tests show clogging just short of 10 units; in bedside practice an additional period of less than 30 to 60 minutes beyond the time at which the terminal flow rate as defined above (1.75 cc/minute) was reached, would pass 10 units; this would in practice normally be aided by increasing the bag height above 102 cm. Thus only one of the 16 tests might have caused some PC to remain in the bag unused. If, however, the tests had been based upon use of a smaller $A_c$ than 62.1 cm$^2$, for example on 50 cm$^2$, it is estimated that four of the sixteen tests would have resulted in only partial delivery. If $A_c$ had been 40 cm$^2$, the results would have been even worse, probably increasing the proportion of incomplete deliveries to about one half of the tests. Thus the preferred minimum effective flow area is about 60 cm$^2$, 50 cm$^2$ is less preferred, and 40 cm$^2$ is still less preferred.

When a single approximately 55 ml unit of platelets is to be processed, an effective flow area in excess of about 6 cm$^2$ is most preferred, since the volume passed is about one tenth that of a ten unit pool of PC.

In Table 2, data for examples 25–50 are presented. Media used were in the thickness range of 0.33 to 0.36 cm. Bulk densities $\rho$ were in the range 0.42 to 0.46 g/cc. Surface area $A_f$ was 0.53 M$^2$/g, and the corresponding fiber diameter 5.5 μm. All of the tests were run using two day old PC. No clogging was experienced. Average efficiency is very close to 100%; the results for the ten unit tests show an average 1000 fold reduction in leucocyte concentration, while the average reduction is 10000 fold for the six and eight unit tests. Recovery averages for the 6, 8 and 10 unit tests are respectively 81.3, 84.5 and 87%, for an overall average of 84.3%, or stated otherwise, a loss of 15.7%. Since the average thickness is 0.332 cm, and the average apparent density is 0.425 g/cc, corresponding to a voids volume of $$100\left(1 - \frac{.425}{1.38}\right) = 69.2\%,$$

fluid hold up within the porous medium is, on average, 0.692×0.332×62.1 = 14 cc. This represents a loss of PC due to hold up within the medium, based on an average eight unit PC transfusion of 14/440×100=3.2%, and increases the average loss for examples 25–50 to 15.7+3.2=18.9%. Similar calculations may be made for the examples which follow.

In Table 3, examples 51–64 are presented. Media used were all 0.19 cm thick, with a bulk density $\rho$ of 0.43 grams/cc. Surface area $A_f$ was 0.67M$^2$/gram, and the corresponding fiber diameter 4.3 $\mu$m. Except as noted, all the tests were run using two day old PC. No clogging was experienced. Average efficiencies are lower than for examples 25–50, reflecting the lower average FSA available for removal of leucocytes by adsorption, 3.4M$^2$ compared with 4.7M$^2$ for examples 25–50.

In Table 4 and Table 5, examples 65–75 and 76–93 are presented. Fiber surface area/gram $A_f$, fiber diameter, and total fiber surface area FSA are substantially equal on average to examples 51–64. Bulk density $\rho$ varies respectively for Tables 3, 4 and 5 from 0.43 g/cc to 0.39 g/cc to 0.36 g/cc. Average recovery varies successively from 82.3 to 87.7 to 90.4%, indicating that recovery improves as density is decreased. For this reason, it is seen that when using $A_f$=0.67 (4.3 $\mu$m average fiber diameter), while a density of 0.43 g/cc yields satisfactory results, a density below about 0.36 g/cc is preferred. The corresponding pore diameters are:

| Table No. | Average pore diameter, $\mu$m |
|---|---|
| 3 | 3.4 |
| 4 | 3.6 |
| 5 | 3.8 |

Since the Table 3 conditions cause some reduction in platelet recovery, it is preferred that pore diameter exceed 3.4 $\mu$m, and more preferably that pore diameter exceed 3.8 $\mu$m.

Filters with good efficiency and recovery can be made using larger pore diameters. Such filters have the disadvantage that the filtering elements are larger, hence the volume of PC held up within the filter element increases. For this reason it is preferred that the pore diameter be not larger than necessary to obtain maximum recovery of PC, for example less than about 10 to 15 $\mu$m. If the pore diameter were increased above about 15 to 30 $\mu$m, it may become possible for some leucocytes to pass through the filter without ever contacting a fiber on which they could be absorbed, thereby reducing efficiency. It is, therefore, preferred that the pore diameter not exceed 15 $\mu$m, and is more preferred that it not exceed 10 $\mu$m and still more preferred that it not exceed 6 $\mu$m, i.e. a preferred range is from about 3.8 to about 6 $\mu$m.

Notably, in this series, the efficiency increases from 99.0 to 99.4% between 0.43 and 0.39 g/cc bulk density, and from 99.4 to 99.5% between 0.39 and 0.36 g/cc. Further, these efficiency improvements occur as the pore size is increased, from 3.4 to 3.8 $\mu$m. These observations indicate that leucocyte removal is primarily if not completely a function of surface area, and thus that the principal or sole mechanism of leucocyte depletion is adsorption.

In Table 6 presenting examples 94–110, preformed elements made with larger fiber surface area, $A_f$, which smaller fiber diameter, and with narrower fiber diameter distribution were used. Fiber surface area $A_f$ was 1.1M$^2$/g (2.6 $\mu$m average fiber diameter), and average FSA was 3.2M$^2$. Thickness was equal to that of examples 65–75, but the average bulk density of 0.232 g/cc for examples 94–110 is 40% lower than the 0.39 average of 65–75, a change required to obtain the same pore size range when using 2.6 $\mu$m as opposed to 4.3 $\mu$m diameter fibers.

The 3.2M$^2$ average FSA of examples 94–110 is less than the 3.3M$^2$ average for examples 65–75, yet efficiency is better.

Remarkably, in examples 94–110 every efficiency measurement showed 100% removal, and the average recovery was a very high 94.2%. Contrasted with these data, earlier tests run using wider range fiber media with higher FSA values, had lower and more variable efficiency, as well as lower recovery.

Loss due to hold up within the elements of examples 94–110 is only 11.3 cc, or 2.6% based on 440 cc of PC, for an overall recovery of 91.6%.

Table 7 presents examples 111–121. The media characteristics are identical to those of Table 6, except with respect to CWST, which is lower. These examples, like those of Table 6, are arranged in order of ascending density. Calculated combined average recovery for ten elements including the five lowest density elements from each of Tables 6 and 7 is 93.6%. The similar value for the ten elements including the five highest density elements from each of the tables is 93.7%. Thus, over the range from about 0.19 to about 0.32 g/cc, recovery is seen not to be affected by density. Similarly, pore diameter variation from about 3 to about 4 $\mu$m appears not be affect recovery.

Examples 108–110 and 117–121, all with FSA in excess of 3.8M$^2$/g, represent a preferred form of this invention. The remainder of examples 25 through 116 represent only slightly less preferred forms of this invention, and examples 1 to 24 are still less preferred. Nevertheless, all of these examples perform better than any commercially available filter.

The efficiency data of Tables 6 and 7 appear to indicate that while quite good results can be gotten with FSA as low as 2.5 to 2.8M$^2$, better results are obtained with FSA larger than 3.0 to 3.3M$^2$. Thus, while FSA as low as 2.5M$^2$ is satisfactory, use of areas larger than 3M$^2$ is preferred, use of areas larger than 3.4M$^2$ is more preferred, and values in excess of 3.8M$^2$ are still more preferred. A range of from about 2.5 to about 4.0M$^2$ may be used with 3.3 to 4.0M$^2$ being preferred.

In Table 8 presenting examples 122–141, the test samples are essentially equal to those of examples 94–121, except with respect to the monomer used for grafting. Whereas all of the preceding examples were grafted using 0.43% HEMA together with 0.082% of MAA, examples 122–132 were grafted using only 0.43% HEMA. The advantage of combining 0.082% of MAA with 0.43% HEMA may be seen by comparing the data of Tables 6 and 7 with those of Table 8:

| Table | Example No's | MMA content of grafting solution, % | Average efficiency | Average recovery |
|---|---|---|---|---|
| 6 | 94–110 | .082 | 100 | 94.2 |
| 7 | 111–121 | .082 | 99.8 | 93.4 |
| 8 | 122–141 | zero | 87.0 | 78.1 |

While the Table 8 data compare poorly with the preceding examples, it should be remembered that Table 8 data are better than those for any unit now commercially available, and further that devices for leucocyte depletion marketed hitherto are not at all suited for bedside service.

Whereas all examples prior to those of Table 8 combined 0.43% HEMA with 0.082% MAA, so that the acid monomer ratio with respect to HEMA is 0.19, the examples of Table 9 combined 0.43% HEMA with 0.164% MAA, for a ratio of MAA to HEMA of 0.38. As may be seen in Table 9, a result of this change is a decrease in average recovery to 81.5%.

In Table 10 examples 155–158 are presented. In this group, the acid monomer ratio was further increased, from 0.38 to 0.64; as may be seen, recovery is further adversely affected, falling to an average of 58.1%.

Figure 5:
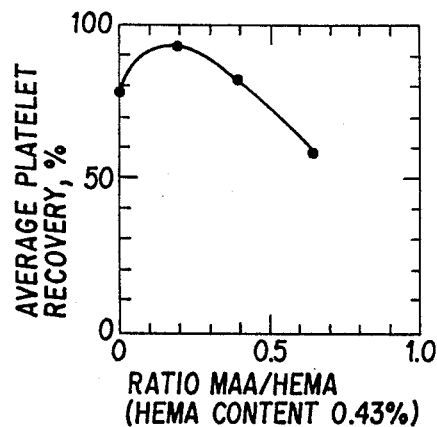
FIG. 5 is a graphical representation of the relationship between the percentage of platelets recovered after passage through a filter of the preferred form of this invention, and the ratio of methacrylic acid monomer (MAA) to hydroxyethyl methacrylate monomer (HEMA) in the grafting solution used to surface modify the polybutylene terephthalate fibers used to make filter medium.

These data are plotted in FIG. 5, showing that the optimum MAA ratio for use with 0.43% HEMA is about 0.18, or more generally, in the range of about 0.05:1 to 0.35:1, within a broader range of 0.01:1 to 0.5:1.

Table 11 presents data illustrating the effect of altering the HEMA content of the grafting solution from 0.11 to 0.7%, while maintaining the MAA content at a 0.19 ratio with respect to HEMA.

Example 158a is the average of four tests in which the HEMA content of the grafting solution was 0.11%. Similarly, example 159 is the average of four tests with HEMA content of 0.22%. Example 160 is the average of the seventeen examples of Table 6, with HEMA content of 0.43%. Example 161 is the average of sixteen examples with HEMA content of 0.54%. Example 162 is the average of ten examples with HEMA content of 0.70%.

Figure 6:
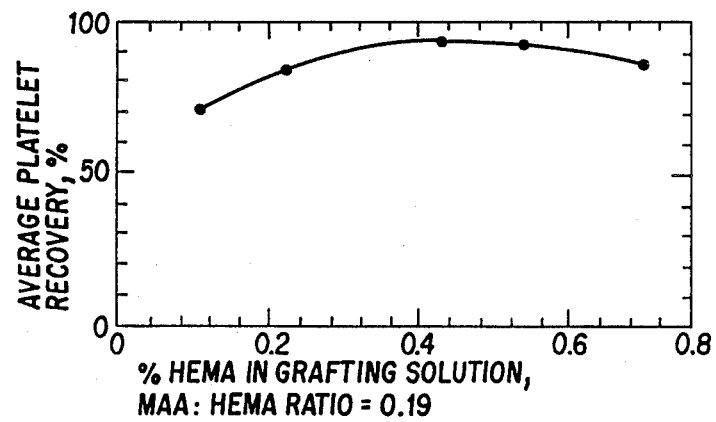
FIG. 6 is a graphical representation of the relationship between platelet recovery and the percentage of HEMA in the grafting solution used, when the MAA:HEMA ratio is 0.19:1.

The data of Table 11 are plotted in FIG. 6, where it is seen that platelet recovery is highest in the range from about 0.4 to 0.5 weight %, and that recoveries in excess of 90% are obtained in the range from about 0.28 to about 0.65 weight %. While these are respectively the most preferred and more preferred ranges, it should be recognized that each of the five examples provides better recovery than any similar device now commercially available, along with leucocyte depletion ranging from about a 300 fold to better than a 1000 fold reduction.

The tests of which example 159 is the average primed very slowly, and those of example 160 primed even more slowly. Both sets of tests primed significantly more slowly than any other example of this invention.

Thus a preferred lower level for HEMA content together with an MAA-HEMA weight ratio in the grafting monomer of 0.19 to 1 is 0.1%, and a more preferred lower limit is 0.2%. A preferred range is 0.28 to 0.65,% and a more preferred range is 0.4 to 0.5%.

These preferred ranges may vary if parameters such as the MAA:HEMA ratio were varied from 0.19 to 1, or if the grafting conditions were changed, for example, by using higher or lower starting concentration and changing the irradiation or other activating conditions. Such ranges would be within the scope of this invention.

Insofar as CWST affects platelet recovery in the examples of Table 11, it may be seen that a CWST in excess of 90 dynes/cm is preferred, and that a CWST of 95 dynes/cm or higher is more preferred.

As noted above, platelet recovery peaks out at about 0.4 to 0.5% HEMA content in FIG. 6; by what may be an extraordinary coincidence, efficiency of leucocyte removal also peaks in a range of about 0.22 to 0.7% HEMA, making this a preferred range with respect to efficiency.

As little as 0.1% of HEMA in the grafting solution is theoretically more than sufficient to provide a complete monomolecular coating on a 2.6 μm diameter fibrous web immersed in it and then exposed to activation by an external energy source. Hence, it can be deduced that the HEMA-MAA deposited on the fiber in the examples above may not be evenly distributed, and for this reason an excess of monomer is required to achieve complete coverage. More uniform coverage might, for example, be obtained by altering the grafting method with respect to the type of energizing source, or with respect to time of exposure to the energy source, or with respect to intensity of the source. Also, other monomers may be found to achieve the high CWST values required, along with optimal recovery and efficiency. In these ways, it may be possible to achieve the preferred degree of surface modification with less than 0.1% of HEMA and other than 0.019% of MAA or other cationic polymer. It should be understood that products which may be achieved by such means fall within the scope of this invention.

Example 163 presented in the following paragraphs, illustrates the viability and continued effectiveness of PC processed using the devices of this invention after transfusion into a patient; it also establishes that the activity in vivo of platelets after transfusion remains normal or close to normal. The filters used in Example 163 were B size assemblies which except for diameter were equal to examples 25–50. The research on which example 163 is based is expected to be published in or very close to the wording below, under the authorship of T. S. Kickler, W. R. Bell, P. M. Ness, H. Drew, and D. B. Pall; The Johns Hopkins University School of Medicine, Baltimore, MD and the Pall Corporation, Glen Cove, N.Y., U.S.A.:

Removal of leucocytes (WBC) from platelets may reduce alloimmunization to WBC antigens. We evaluated a new surface modified fibrous polyester filter that requires no special processing of pooled platelet concentrates and can be used at the bedside. Our studies were designed to measure WBC removal, platelet function, in vitro platelet recovery, and in vivo platelet survival. WBC counts were done manually and showed a mean removal of 99.7%±0.56, n=38. Platelet recovery was 85.4%±5.4, n=38. Clot retraction and phase microscopy morphology were unaffected. Using epinephrine, ADP, collagen, and ristocetin in platelet aggregation studies on 15 samples, there was no difference in the prefiltration versus the post-filtration specimens.

111-Indium platelet survival studies were done using autologous platelet concentrates in 5 volunteers. Immediately following their preparation, the platelets were filtered and labeled with 111-Indium oxine. After transfusion, samples were collected for 10 days, and results analyzed using the gamma function curve fitting model. The platelet life span for the 5 donors was 8.2, 8.1, 7.0, 9.2, 8.5 days (normal: 8.7±1.1 days).

These studies indicate that the filter efficiently removes WBC without substantially decreasing platelet number or altering platelet function or survival. This device offers the potential of reducing platelet transfusion reactions and alloimmunization.

Thus, the products of this invention have been proven to have great ease of use because of their adaptibility to use at bedside, easy wettability and consequent rapid priming, very small loss of PC due to hold up within the device, together with extraordinarily high leucocyte removal efficiency and platelet recovery. In addition it has been demonstrated in vivo that the platelets passed through the device into a patient suffer no measurable loss of effectiveness, nor any loss of their normal life span in the human body.

In preceding sections of this application filters were prepared by exposing otherwise identical fibrous media to grafting solutions containing in each case 0.43% HEMA, but with MAA varying over a wide range, from zero to about 0.28%. These filters were each used in a number of platelet concentrate filtration tests, and the average proportion of platelets recovered was determined, along with the average efficiency of leucocyte removal. In this way, it was established that the most favorable result was obtained with the ratio of MAA to HEMA in the range of about 0.05 to 1 to 0.35 to 1, or more generally within the broader range of 0.01-1 to 0.5-1.

While testing of the grafted product by passing platelet concentrate and analyzing the effluent is a satisfactory method for exploring to determine the optimal range, this method is not convenient for use in routine production quality control for the following reasons:

(a) Platelet concentrate is very costly, multiple tests are needed, and many units are required for each test. For example, if each test were run using a pooled lot of 10 units of platelets, at 1988 USA prices the expenditure to purchase platelets would exceed $400 per test. In addition, each test requires a considerable investment in labor, in the neighborhood of one person-day per test.

(b) Due to variability of the platelet concentrate, with no two units exactly alike, a large number, e.g., at least five or preferably more must be run in order to obtain meaningful average values for the efficiency of platelet recovery.

Thus, a quickly and economically performed test which would correlate well with platelet recovery performance is seen to be desirable, and such a test is an objective of this invention.

As noted above, the addition of MAA to HEMA in the grafting solution was found to cause the product to have a higher negative zeta potential compared with material grafted with HEMA only. Accordingly, zeta potential measurement was considered as an option for evaluating grafted fibrous media. Zeta potential can be measured by streaming potential, or by suspending fragments of fibers in an electrolyte and then using a microscope to measure migration rate of the fibers in an electrical field. Both methods require a skilled operator, are quite slow, and often produce inconsistent data.

One reason for the inconsistency of the zeta potential measurements is that when PBT fibrous medium is grafted using solely HEMA as the monomer the product has negative zeta potential. The effect on zeta potential of adding MAA to the grafting solution is thus incremental, rather than absolute. This decreases the sensitivity of such measurements.

We have discovered a simple analytical method which can be rapidly performed and which correlates well with the MAA content of the grafting solution and with the platelet recovery performance of the grafted fibrous PBT. The basis of this method is the passage through a column of known weight of the porous medium of a solution of a dye which is substantive to substances which contain anionic groups on their surfaces. Such a dye should preferably having a high absorbancy or reflectivity for a visually recognized or photometrically measured wave length of light. The absorbed wave length must be in the visible region of the spectrum if visual observation is the criterion, but can be in the ultra-violet or infra-red spectrum if spectrophotometry is used to detect the presence of the dye.

In either case, a solution of the dye is passed through a column of the filter medium at a rate sufficiently low to allow the dye solution to equilibrate with the grafted medium. If the dye selected is one with a high positive zeta potential, such as is exhibited by dyes whose active group or groups may be amine, or more preferably quaternary ammonium group or groups, it will be ionically adsorbed to carboxyl or other anionic groups on the surfaces of the fiber. When flow is first started, the dye is completely adsorbed, and clear liquid, essentially pure water, emerges. When all of the surface groups near to the entry of the column have adsorbed dye molecules and are saturated, dye progresses to the next level of the column, which is similarly saturated, and this process continues until solution containing the dye issues from the end of the column. The appearance of color, or absorption of light waves by the dye if spectrophotometry is used, signals that the contents of the column have been saturated. The volume of dye passed to this point is a measure of the surface population of carboxyl or other anionic groups at the surface of the porous medium.

As the dye advances through the column, the front has a significant band width, due to the time required for diffusion to occur from the dye solution to the fiber surfaces, as well as due to diffusion of the dye in a vertical direction. This band width can be reduced to less than about 1 mm in width by selecting appropriate flow rate and dye concentration, and by evacuating the column prior to first filling with liquid. If there is any possibility that the medium being tested has been exposed to metal ions while in the process of being grafted and thereafter washed free of residual grafting fluid, the media used for this test should be restored to the acid form by exposure to a weak acid solution, then washed free of acid using deionized water. In order to assure reproducible results, the column height should be at least 0.7 cm, and the density of the column equal to about 0.23 grams per cc.

The column can be prepared from porous medium in sheet-form by cutting the appropriate number of discs and assembling them into a preferably transparent tube of inside diameter about 1 to 1.5 cm. Discs must be cut such that their outer edge is perpendicular to the plane of the disc, each disc forming a true right cylinder about 1% larger than the inside diameter of the transparent tube.

A number of dyes are available which are well suited for this purpose. We have used a quaternized diamine, Safranine O, of which the structure is shown below:

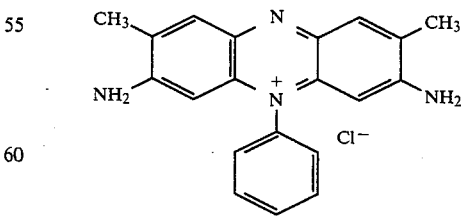

As Safranine O is used as a biological stain, it is readily available in many laboratories, and for this reason is a convenient choice.

Figure 7:
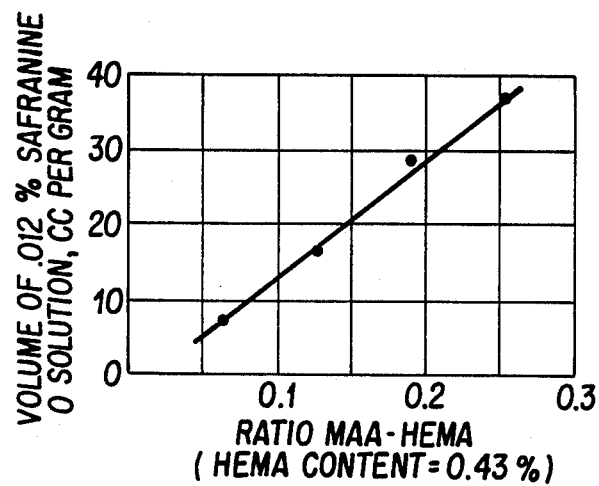
FIG. 7 is graphical representation of the relationship between the volume of aqueous solution of a dye, Safranine O, adsorbed from solution in water, expressed as cubic centimeters of 0.012% solution per gram of 2.5 $\mu$m average diameter fiber, when passed at 0.38 cm per minute through a 0.7 cm high column of fibrous medium, the fibers having been modified by radiation grafting in a base solution containing 0.43% of HEMA together with varying proportions of MAA.

Examples 164–167 show the relationship between the volume of a 0.012% Safranine O solution adsorbed per gram of fiber, and the proportion of MAA based on the HEMA content added to 0.43% of HEMA in the grafting solution used to modify the fiber surface. The resulting data are shown in FIG. 7. This relationship is seen to be linear.

Media prepared in the identical manner as those used in examples 164 to 167 were grafted in a manner paralleling the filters used in examples 111-154, except that (a) the average fiber surface area was 3 square meters,
(b) average fiber diameter was 2.5 μm,
(c) average density was 0.22 g/cc,
(d) fiber size distribution was slightly narrower,
(e) the radiation grafting was done in production scale apparatus, as opposed to laboratory scale used in the earlier examples, and
(f) HEMA content remained at 0.43%, while MAA:-HEMA ratio was varied to include 0.064, 0.13, 0.19 and 0.25%.

The resulting filters were each used in twelve or more tests at each MAA-HEMA ratio to pass platelet concentrate equivalent to respectively 6, 8 and 10 units, yielding for each test three values for platelet recovery, and three for leucocyte removal efficiency. The three platelet recovery percentages obtained in each of the twelve or more tests were averaged with results listed in Table 13. The leucocyte removal averages were similarly determined, and were all essentially equal, the range for the four different MAA concentrations being 99.84% to 99.91%.

The platelet recovery data of examples 168-171 were plotted against the proportion of MAA used in the grafting solution relative to 0.43% HEMA (FIG. 8), and show a preferred range of MAA to HEMA ratio in the grafting solution relative to the HEMA content of 0.43% of 0.05 to 0.25.

Figure 8:
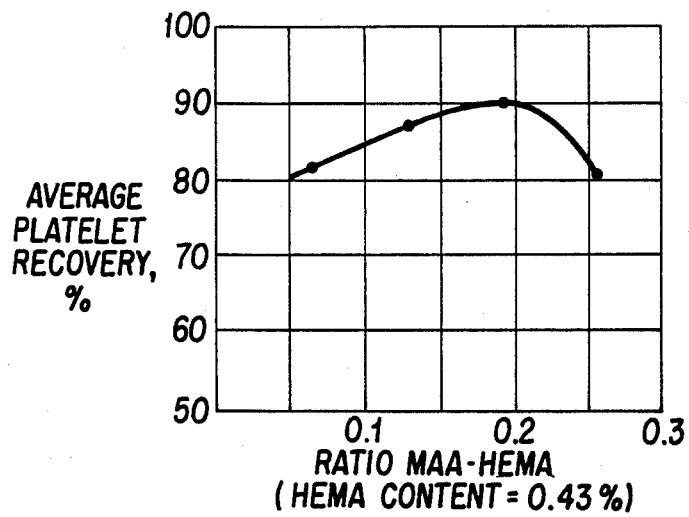
FIG. 8 is a graphical representation of the relationship between the proportion of MAA in the grafting solution relative to 0.43% of MEMA, and the average recovery of platelets when 6, 8 and 10 equivalent units of platelets were passed through a filter of this invention.

The minor difference in preferred range between the data of FIGS. 5 and 8 are believed to be due to not unexpected changes in the product obtained when changing from laboratory scale (FIG. 5) to production scale (FIG. 8), and may reflect as well the use of fibers with narrower size distribution. Both FIG. 5 and FIG. 8 show that a ratio of about 0.19 is optimal. This difference serves to underline one of the advantages of controlling product characteristics by the dye adsorption method.

Figure 9:
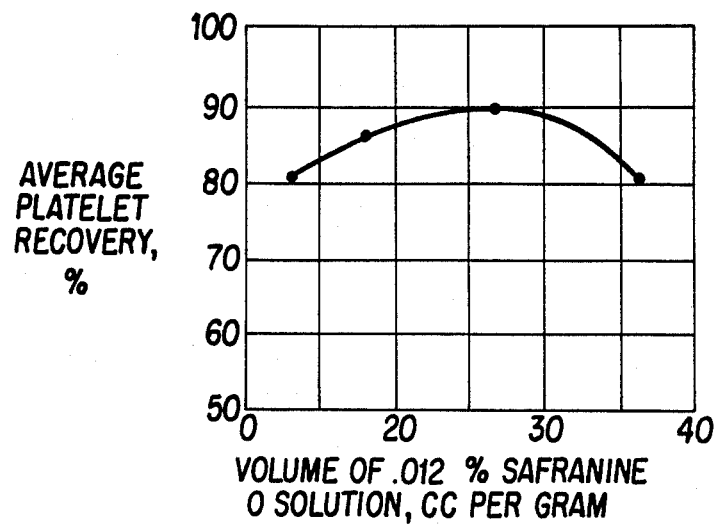
FIG. 9 is a graphical representation of the relationship between the recovery of platelets when platelet concentrate is passed through a filter of this invention comprising fibers radiation grafted in a solution containing 0.43% of HEMA together with varying proportions of MAA, and the volume of 0.012% Safranine O solution passed prior to color breakthrough expressed as cubic centimeters of solution per gram of 2.5 $\mu$m diameter fiber, when passed at 0.38 cm per minute through a 0.7 cm high column of fibers equal to those used in a platelet recovery test.

The platelet recovery data of examples 168-171 are plated against Safranine O adsorption in FIG. 9, and is seen to indicate a preferred range of about 10 to 35 cc of 0.12% Safranine O per gram, and a more preferred range of about 17 to 34 cc of 0.012% Safranine O per gram.

TABLE 1

| Example No. | Age of Platelets, Days | No. of PC Units Passed Prior to Clogging |
|---|---|---|
| 1 | 7.5[1] | 2 |
| 2 | 7.5 | 1 |
| 3 | 7 | 10 |
| 4 | 7 | 8 |
| 5 | 6 | >10 |
| 6 | 6 | 8 |
| 7 | 6 | >10 |
| 8 | 6 | >10 |
| 9 | 5 | >10 |
| 10 | 5 | >10 |
| 11 | 5 | 4 |
| 12 | 5 | >10 |
| 13 | 5 | >10 |
| 14 | 5 | >10 |
| 15 | 5 | >10 |
| 16 | 5 | >10 |
| 17 | 5 | >10 |
| 18 | 5 | 9 |
| 19 | 5 | >10 |
| 20 | 5 | 9 |
| 21 | 5 | 9 |
| 22 | 5 | >10 |
| 23 | 5 | >10 |
| 24 | 5 | >10 |

[1]Pooled PC, 50% each of units 7 day and 8 day old.

TABLE 2

Two Day Old PC, Acid Monomer Ratio 0.19

| A Example No. | B t, cm | C ρ g/cm | D CWST dynes/cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 25 | .36 | 0.42 | 98 | 3.4 | 5.0 | 99.8 | 99.8 | 99.3 | 99.63 | 88.0 | 89.0 | 89.4 | 88.8 |
| 26 | " | " | " | " | " | 100 | 100 | 100 | 100 | 87.3 | 89.4 | 90.3 | 89.0 |
| 27 | .33 | 0.46 | 97 | 3.4 | 5.0 | 100 | 100 | 99.9 | 100 | 75.3 | 79.0 | 81.8 | 78.7 |
| 28 | " | " | " | " | " | 100 | 100 | 99.9 | 99.97 | 88.1 | 91.2 | 93.1 | 90.8 |
| 29 | " | 0.42 | 110 | 3.6 | 4.6 | 100 | 100 | 100 | 100 | 84.8 | 86.0 | 89.2 | 86.7 |
| 30 | " | " | " | " | " | 100 | 100 | 100 | 100 | 89.8 | 93.0 | 94.9 | 92.6 |
| 31 | " | " | " | " | " | 100 | 100 | 100 | 100 | 83.9 | 87.5 | 89.3 | 86.1 |
| 32 | " | " | " | " | " | 100 | 100 | 100 | 100 | 74.8 | 79.5 | 83.2 | 79.2 |
| 33 | " | " | " | " | " | 100 | 100 | 100 | 100 | 66.1 | 76.7 | 81.0 | 74.6 |
| 34 | " | " | " | " | " | 100 | 100 | 99.8 | 99.93 | 77.0 | 81.2 | 83.0 | 80.4 |
| 35 | " | " | " | " | " | 100 | 100 | 100 | 100 | 81.5 | 83.5 | 86.4 | 83.8 |
| 36 | " | " | 97 | " | " | 100 | 100 | 100 | 100 | 84.5 | 88 | 89.5 | 87.3 |
| 37 | " | " | " | " | " | 100 | 100 | 100 | 100 | 91.5 | 91.5 | 93.0 | 92.0 |
| 38 | " | " | " | " | " | 100 | 100 | 100 | 100 | 83 | 85 | 87.7 | 85.3 |
| 39 | " | " | " | " | " | 100 | 100 | 100 | 100 | 80 | 83 | 86.0 | 83.0 |
| 40 | " | " | " | " | " | 100 | 100 | 100 | 100 | 91 | 92.5 | 94.1 | 92.3 |
| 41 | " | " | " | " | " | 100 | 100 | 100 | 100 | 86.5 | 87.1 | 89.5 | 87.7 |
| 42 | " | " | " | " | " | 100 | 100 | 100 | 100 | 92.7 | 94.4 | 95.5 | 94.2 |
| 43 | " | " | " | " | " | 100 | 100 | 99.6 | 99.87 | 93.3 | 93.0 | 94.0 | 93.4 |
| 44 | " | " | " | " | " | 100 | 100 | 100 | 100 | 81.8 | 84.5 | 86.0 | 84.1 |
| 45 | " | " | " | " | " | 100 | 100 | 100 | 100 | 89.9 | 90.8 | 92.3 | 91.0 |
| 46 | .32 | 0.45 | 97 | 3.3 | 4.7 | 100 | 99.9 | 99.0 | 99.63 | 75.0 | 78.8 | 83.5 | 79.1 |
| 47 | " | " | " | " | " | 100 | 100 | 99.9 | 100 | 72.2 | 77.2 | 83.5 | 77.6 |
| 48 | .33 | 0.42 | 110 | 3.5 | 4.6 | 100 | 100 | 100 | 100 | 75.0 | 82.0 | 84.0 | 80.5 |
| 49 | " | " | " | " | " | 100 | 100 | 100 | 100 | 63.6 | 69.1 | 73.4 | 68.7 |
| 50 | " | " | " | " | " | 100 | 100 | 100 | 100 | 56.3 | 62.9 | 68.0 | 62.4 |

TABLE 2-continued

Two Day Old PC, Acid Monomer Ratio 0.19

| A Example No. | B t, cm | C ρ g/cm | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| Average | 0.332 | .425 | 102 | 3.5 | 4.7 | 99.99 | 99.99 | 99.90 | 99.96 | 81.3 | 84.5 | 87.0 | 84.3 |

TABLE 3

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 51 | 0.19 | .43 | 110 | 3.4 | 3.4 | 100 | 100 | 99.2 | 99.7 | 81.9 | 83.0 | 87.5 | 84.1 |
| 52 | " | " | " | " | " | 100 | 99.4 | 87.5 | 95.6 | 71.5 | 79.2 | 78.9 | 76.5 |
| 53 | " | " | " | " | " | 100 | 97.6 | 95.2 | 97.6 | 93.3 | 84.6 | 85.1 | 87.7 |
| 54 | " | " | " | " | " | 100 | 100 | 98.7 | 99.6 | 84.6 | 82.0 | 84.3 | 83.6 |
| 55 | " | " | " | " | " | 100 | 99.5 | 97.2 | 98.9 | 76.7 | 78.2 | 79.5 | 78.7 |
| 56 | " | " | " | " | " | 100 | 100 | 97.7 | 99.2 | 78.9 | 79.3 | 80.4 | 79.5 |
| 57 | " | " | " | " | " | 100 | 100 | 100 | 100 | 88.7 | 86.5 | 86.4 | 87.2 |
| 58 | " | " | " | " | " | 100 | 100 | 100 | 100 | 78.8 | 81.4 | 83.6 | 81.3 |
| 59* | " | " | " | " | " | 100 | 100 | 100 | 100 | 89.3 | 85.2 | 88.1 | 87.5 |
| 60* | " | " | " | " | " | 100 | 100 | 100 | 100 | 76.9 | 88.5 | 92.3 | 85.9 |
| 61 | " | " | " | " | " | 100 | 95.5 | 92.8 | 96.1 | 86.0 | 75.8 | 83.6 | 81.8 |
| 62 | " | " | " | " | " | 100 | 100 | 100 | 100 | 78.3 | 81.4 | 82.4 | 80.7 |
| 63 | " | .44 | " | 3.3 | 3.5 | 100 | 100 | 98.8 | 99.6 | 66.2 | 76.2 | 79.9 | 74.1 |
| 64 | " | .44 | " | " | " | 100 | 99.8 | 99.4 | 99.7 | 84.6 | 82.0 | 84.3 | 83.6 |
| Average | 0.19 | 0.43 | 110 | 3.4 | 3.4 | 100 | 99.4 | 97.6 | 99.0 | 81.1 | 81.7 | 84.0 | 82.3 |

*Three day old PC

TABLE 4

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 65 | 0.20 | .39 | 110 | 3.6 | 3.3 | 100 | 99.7 | 98.6 | 99.4 | 96.5 | 86.1 | 87 | 89.9 |
| 66 | " | " | " | " | " | 100 | 97.6 | 95.2 | 97.6 | 87.4 | 91.7 | 90.7 | 89.9 |
| 67 | " | " | " | " | " | 100 | 100 | 98.9 | 99.6 | 97.0 | 91.0 | 85.7 | 91.2 |
| 68 | " | " | " | " | " | 100 | 100 | 100 | 100 | 92.2 | 92.5 | 92.3 | 92.3 |
| 69 | " | " | " | " | " | 100 | 96.7 | 97.8 | 98.1 | 96.2 | 93.2 | 92.9 | 94.1 |
| 70 | " | " | " | " | " | 100 | 100 | 100 | 100 | 78.8 | 81.4 | 83.6 | 81.3 |
| 71 | " | " | " | " | " | 100 | 100 | 100 | 100 | 74.0 | 84.5 | 83.3 | 80.5 |
| 72* | " | " | " | " | " | 100 | 98.5 | 97.5 | 98.7 | 74.5 | 73.4 | 75.0 | 74.3 |
| 73* | " | " | " | " | " | 100 | 100 | 100 | 100 | 85.9 | 93.0 | 91.0 | 90.0 |
| 74* | " | " | " | " | " | 100 | 100 | 100 | 100 | 95.7 | 90.7 | 90.4 | 92.3 |
| 75 | " | " | " | " | " | 100 | 100 | 98.8 | 99.6 | 86.8 | 88.4 | 91.7 | 89.0 |
| Average | 0.20 | .39 | 110 | 3.6 | 3.3 | 100 | 99.3 | 98.8 | 99.4 | 87.7 | 87.8 | 87.6 | 87.7 |

*Three day old PC

TABLE 5

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 76 | 0.211 | 0.363 | 110 | 3.9 | 3.2 | 100 | 98.6 | 98.4 | 99.0 | 91.4 | 89.3 | 89.4 | 90.0 |
| 77 | " | " | " | " | " | 99.0 | 98.3 | 97.6 | 98.3 | 86.0 | 89.6 | 87.6 | 87.7 |
| 78 | " | " | " | " | " | 100 | 97.4 | 96.5 | 98.0 | 100 | 93.5 | 92.0 | 95.2 |
| 79* | " | " | " | " | " | 98.5 | 98.5 | 95.6 | 98.2 | 99.8 | 94.4 | 89.8 | 94.7 |
| 80 | 0.218 | 0.376 | " | " | 3.4 | 100 | 100 | 100 | 100 | 92.8 | 89.9 | 92.3 | 91.6 |
| 81 | " | " | " | " | " | 100 | 100 | 99.5 | 99.8 | 94.0 | 94.4 | 93.8 | 94.1 |
| 82 | 0.221 | 0.378 | " | 3.8 | 3.5 | 100 | 100 | 99.8 | 99.9 | 88.3 | 87.4 | 88.9 | 88.2 |
| 83 | " | " | " | " | " | 100 | 100 | 98.7 | 99.6 | 97.3 | 95.1 | 93.3 | 95.3 |
| 84 | 0.228 | 0.352 | " | 3.9 | 3.3 | 100 | 100 | 100 | 100 | 90.1 | 91.6 | 91.8 | 91.2 |
| 85 | 0.234 | 0.341 | " | " | 3.3 | 100 | 100 | 97.6 | 99.2 | 87.0 | 87.4 | 86.4 | 86.9 |
| 86 | 0.233 | 0.371 | " | 3.8 | 3.4 | 100 | 100 | 100 | 100 | 91.7 | 92.8 | 92.9 | 92.5 |
| 87 | " | 0.367 | " | " | " | 100 | 100 | 100 | 100 | 83.1 | 84.0 | 85.0 | 84.1 |
| 88 | " | 0.352 | " | " | " | 100 | 100 | 99.7 | 99.9 | 92.4 | 90.5 | 92.1 | 91.7 |
| 89 | " | 0.350 | " | " | " | 100 | 100 | 100 | 100 | 97.5 | 93.7 | 93.5 | 94.9 |
| 90 | " | 0.361 | " | " | " | 100 | 100 | 99.4 | 99.8 | 82.1 | 86.6 | 88.2 | 85.6 |
| 91 | " | 0.372 | " | " | " | 100 | 100 | 100 | 100 | 91.1 | 87.7 | 86.1 | 88.3 |

TABLE 5-continued

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 92 | " | 0.368 | " | " | " | 100 | 100 | 100 | 100 | 91.4 | 85.3 | 88.4 | 88.4 |
| 93 | " | 0.371 | " | " | " | 100 | 100 | 100 | 100 | 86.4 | 86.2 | 89.0 | 87.2 |
| Average | 0.22 | 0.36 | 110 | 3.8 | 3.4 | 99.9 | 99.6 | 99.0 | 99.5 | 91.2 | 90.0 | 90.0 | 90.4 |

*Three day old PC

TABLE 6

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 94* | 0.21 | 0.182 | 107 | 4.2 | 2.5 | 100 | 100 | 100 | 100 | 91.5 | 90.7 | 91.5 | 91.2 |
| 95* | " | " | " | " | " | " | " | " | " | 100 | 93.8 | 88.4 | 94.1 |
| 96* | " | 0.210 | " | 4.0 | 2.9 | " | " | " | " | 100 | 100 | 98.3 | 99.4 |
| 97* | " | 0.211 | " | " | " | " | " | " | " | 98.6 | 92.9 | 91.7 | 94.4 |
| 98* | " | " | " | " | " | " | " | " | " | 93.6 | 94.7 | 91.8 | 93.4 |
| 99 | " | 0.213 | " | " | 3.0 | " | " | " | " | 100 | 99.6 | 93.5 | 97.7 |
| 100* | " | 0.216 | " | 3.9 | " | " | " | " | " | 80.6 | 88.2 | 84.6 | 84.5 |
| 101 | " | 0.217 | 96 | " | 3.0 | " | " | " | " | 100 | 97.1 | 96.4 | 97.8 |
| 102 | " | 0.219 | " | " | 3.1 | " | " | " | " | 100 | 100 | 100 | 100 |
| 103* | " | 0.226 | 107 | 3.6 | 3.2 | " | " | " | " | 87.3 | 93.7 | 89.2 | 90.1 |
| 104* | " | 0.233 | " | " | " | " | " | " | " | 82.7 | 88.5 | 89.5 | 86.9 |
| 105 | " | 0.238 | " | 3.5 | 3.3 | " | " | " | " | 96.6 | 86.9 | 87.6 | 90.4 |
| 106 | " | 0.239 | " | " | " | " | " | " | " | 100 | 99.7 | 91.5 | 97.1 |
| 107 | " | 0.243 | " | " | 3.4 | " | " | " | " | 96.6 | 98.3 | 98.9 | 97.9 |
| 108 | " | 0.283 | " | 3.3 | 3.9 | " | " | " | " | 100 | 100 | 100 | 100.0 |
| 109 | " | 0.309 | " | 3.2 | 4.3 | " | " | " | " | 100 | 94.1 | 92.4 | 95.5 |
| 110 | " | 0.318 | " | 3.2 | 4.4 | " | " | " | " | 93.1 | 90.2 | 87.7 | 90.3 |
| Average | 0.21 | 0.232 | 106 | 3.7 | 3.2 | 100 | 100 | 100 | 100 | 95.3 | 94.6 | 92.6 | 94.2 |

*3 Day old platelets. Balance are two days old.

TABLE 7

2 and 3 Day Old PC, Acid Monomer Ratio 0.19

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 111 | 0.20 | 0.21 | 95 | 4.0 | 2.8 | 100 | 96.4 | 89.9 | 95.4 | 99.4 | 100 | 100 | 99.8 |
| 112 | " | " | " | " | " | " | 100 | 100 | 100 | 100 | 100 | 100 | 100 |
| 113 | " | 0.22 | " | 3.9 | 3.0 | " | " | " | " | 81.2 | 89.2 | 91.1 | 87.2 |
| 114 | " | " | " | " | " | " | " | " | " | 87.4 | 84.8 | 80.3 | 84.2 |
| 115* | " | " | " | " | " | " | " | " | " | 90.8 | 91.4 | 94.2 | 92.1 |
| 116 | 0.21 | 0.23 | " | 3.6 | 3.3 | " | " | 98.5 | 99.5 | 88.5 | 95.8 | 95.2 | 93.2 |
| 117* | 0.22 | 0.30 | " | 3.2 | 4.5 | " | " | 100 | 100 | 96.0 | 92.4 | 92.5 | 93.6 |
| 118* | " | 0.31 | " | 3.1 | 4.6 | " | " | " | " | 81.2 | 89.1 | 91.1 | 87.1 |
| 119* | " | 0.31 | " | " | " | " | " | " | " | 86.7 | 84.8 | 89.9 | 87.1 |
| 120 | " | 0.31 | " | 3.1 | 4.6 | " | " | " | " | 100 | 97.2 | 97.2 | 98.1 |
| 121 | " | 0.33 | " | 3.0 | 4.9 | " | " | " | " | 78.0 | 94.9 | 97.6 | 90.2 |
| Average | 0.21 | 0.26 | 95 | 3.5 | 3.7 | 100 | 99.7 | 98.9 | 99.5 | 89.9 | 92.7 | 93.6 | 92.1 |

*3 Day old Platelets

TABLE 8

Two Day Old PC - No Acid Monomer

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 122 | 0.21 | 0.19 | 101 | 3.9 | 2.7 | 100 | 100 | 100 | 100 | 57.9 | 64.7 | 69.9 | 64.2 |
| 123 | " | 0.20 | " | 3.8 | 2.8 | " | " | " | " | 45.2 | 54.9 | 69.9 | 56.7 |
| 124 | " | 0.21 | " | " | 3.0 | " | " | " | " | 48.3 | 66.3 | 77.2 | 63.9 |
| 125 | " | 0.23 | " | 3.5 | 3.3 | " | " | " | " | 48.0 | 55.5 | 61.1 | 54.9 |
| 126 | " | 0.20 | 116 | 3.8 | 2.8 | " | " | " | " | 61.9 | 68.1 | 72.1 | 67.3 |
| 127 | " | 0.21 | 116 | " | 3.0 | " | " | " | " | 49.4 | 60.8 | 73.8 | 61.3 |
| 128 | " | 0.21 | 116 | " | " | " | " | " | " | 57.2 | 55.5 | 65.1 | 59.3 |
| 129 | " | 0.21 | 116 | " | " | " | " | " | " | 34.3 | 49.7 | 66.4 | 50.1 |
| 130 | " | 0.22 | " | 3.6 | 3.2 | " | 100 | 99.0 | 100 | 100 | 91.5 | 94.3 | 95.3 |
| 131 | " | 0.22 | " | " | " | " | 99.9 | 99.7 | 99.9 | 100 | 96.8 | 96.9 | 97.9 |

TABLE 8-continued

Two Day Old PC - No Acid Monomer

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 132 | " | 0.23 | " | " | " | " | 99.9 | 99.6 | 99.8 | 99.7 | 100 | 100 | 100 |
| 133 | " | 0.22 | 90 | 3.7 | 3.2 | 86.5 | 75.8 | 72.2 | 78.2 | 89.3 | 94.4 | 90.1 | 91.3 |
| 134 | " | " | " | " | 3.2 | 97.0 | 95.3 | 88.5 | 93.6 | 100 | 89.6 | 88.0 | 92.5 |
| 135 | " | " | " | " | " | 85.0 | 70.0 | 65.0 | 73.3 | 100 | 87.0 | 85.3 | 90.7 |
| 136 | " | 0.24 | " | 3.5 | 3.4 | 99.0 | 77.0 | 71.3 | 82.4 | 99.0 | 77.0 | 71.3 | 82.4 |
| 137 | " | 0.23 | 116 | " | 3.3 | 100 | 99.9 | 99.9 | 99.9 | 100 | 93.1 | 95.2 | 96.2 |
| 138 | " | 0.22 | 90 | " | 3.2 | 75.7 | 60.8 | 47.7 | 61.4 | 79.3 | 81.8 | 87.8 | 83.0 |
| 139 | " | " | " | " | " | 70.3 | 55.4 | 43.2 | 56.3 | 87.2 | 85.7 | 85.7 | 86.2 |
| 140 | " | " | " | " | " | 78.4 | 48.7 | 37.8 | 55.0 | 86.8 | 77.3 | 82.5 | 82.2 |
| 141 | " | " | " | " | " | 78.4 | 55.4 | 42.3 | 58.7 | 88.7 | 84.4 | 89.3 | 87.5 |
| Average | 0.21 | 0.22 | 103 | 3.7 | 3.2 | 93.5 | 86.9 | 83.3 | 87.9 | 76.6 | 76.7 | 81.1 | 78.1 |

TABLE 9

Two and Three Day Old PC; Acid Monomer Ratio = 0.38

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 142* | 0.22 | 0.20 | " | " | " | " | " | " | " | 90.7 | 92.2 | 90.6 | 91.2 |
| 143* | 0.21 | 0.21 | " | 3.6 | 3.1 | " | " | " | " | 100 | 92.9 | 88.0 | 93.6 |
| 144* | " | 0.22 | " | " | " | " | " | " | " | 84.6 | 91.3 | 89.2 | 88.4 |
| 145* | 0.22 | 0.22 | " | " | " | " | " | 99.1 | 99.7 | 70.8 | 67.0 | 66.7 | 68.2 |
| 146* | 0.22 | 0.22 | " | " | " | " | " | 92.3 | 97.4 | 96.9 | 80.6 | 82.7 | 86.7 |
| 147* | 0.22 | 0.22 | 94 | 3.5 | 3.3 | 100 | 100 | 100 | 100 | 83.5 | 80.0 | 81.0 | 81.5 |
| 148 | 0.22 | 0.22 | " | " | " | " | " | 100 | 100 | 100 | 90.5 | 85.0 | 91.8 |
| 149 | 0.22 | 0.22 | " | " | " | " | " | " | " | 93.4 | 92.0 | 90.3 | 91.9 |
| 150* | " | 0.22 | " | 3.5 | 3.3 | " | " | " | " | 100 | 94.7 | 89.8 | 94.8 |
| 151 | " | 0.23 | " | " | 3.3 | " | 99.3 | " | " | 78.7 | 71.5 | 62.6 | 70.9 |
| 152 | " | 0.24 | " | 3.4 | 3.4 | 99.9 | 99.2 | 99.0 | 99.4 | 89.4 | 71.5 | 80.5 | 80.5 |
| 153 | 0.21 | 0.24 | " | 3.4 | 3.4 | " | " | 99.9 | " | 43 | 38 | 41.1 | 40.7 |
| 154 | " | 0.25 | " | 3.3 | 3.6 | " | " | 99.5 | 99.8 | 90.8 | 79.7 | 67.8 | 79.4 |
| Average | 0.22 | 0.22 | 94 | 3.5 | 3.3 | 100 | 99.9 | 99.1 | 99.7 | 86.3 | 80.1 | 78.1 | 81.5 |

*Three Day Old PC

TABLE 10

Two Day Old PC, Acid Monomer Ratio 0.64

| A Example No. | B t, cm | C ρ g/cc | D CWST dynes/ cm | E Dp, μm | F FSA, M² | G Efficiency for units passed, % 6 | H 8 | I 10 | J Av. Eff. | K Recovery for units passed, % 6 | L 8 | M 10 | N Av. Rec. |
|---|---|---|---|---|---|---|---|---|---|---|---|---|---|
| 155 | 0.23 | 0.17 | 91 | 3.9 | 2.6 | 100 | 100 | 100 | 100 | 50.7 | 54.7 | 62.1 | 55.8 |
| 156 | 0.23 | 0.17 | " | " | " | " | " | " | " | 75.0 | 70.6 | 67.3 | 71.0 |
| 157 | 0.18 | 0.24 | " | 3.3 | 2.9 | " | " | " | " | 42.9 | 57.1 | 70.1 | 56.7 |
| 158 | 0.18 | 0.24 | " | " | " | " | " | " | " | 33.3 | 48.6 | 64.0 | 48.6 |
| Average | 0.205 | 0.205 | 91 | 3.6 | 2.75 | 100 | 100 | 100 | 100 | 50.5 | 57.8 | 65.9 | 58.1 |

TABLE 11

2 and 3 Day Old PC, Acid Monomer Ratio 0.19

| A Example No. | B % Hema in Monomer | C t, cm | D ρ g/cc | E CWST dynes/ cm | F Dp, μm | G FSA, M² | H Efficiency for units passed, % 6 | I 8 | J 10 | K Av. Eff. | L Recovery for units passed, % 6 | M 8 | N 10 | O Av. Rec. |
|---|---|---|---|---|---|---|---|---|---|---|---|---|---|---|
| 158a | 0.11 | 0.21 | 0.23 | 90 | 3.7 | 3.3 | 100.00 | 99.75 | 99.43 | 99.73 | 49.6 | 58.0 | 60.6 | 71.2 |
| 159 | 0.22 | " | " | 95 | " | " | 100.00 | 100.00 | 99.73 | 99.91 | 85.2 | 81.9 | 86.1 | 84.5 |
| 160 | 0.43 | 0.22 | 0.24 | 102 | 3.6 | 3.4 | 100.00 | 100.00 | 100.00 | 100.00 | 95.3 | 94.6 | 92.6 | 94.2 |
| 161 | 0.54 | 0.21 | 0.23 | 99 | 3.7 | 3.3 | 99.99 | 99.92 | 99.72 | 99.88 | 93.0 | 93.6 | 92.5 | 93.0 |
| 162 | 0.70 | 0.21 | 0.22 | 99 | 3.7 | 3.1 | 99.99 | 99.89 | 99.92 | 99.92 | 86.6 | 87.7 | 86.7 | 87.0 |

TABLE 12

| Example No. | Ratio MAA to 0.43% HEMA | Volume of Safranine O solution adsorbed per gram, cc |
|---|---|---|
| 164 | .064 | 6.7 |
| 165 | 0.13 | 16.0 |
| 166 | 0.19 | 28.6 |

TABLE 12-continued

| Example No. | Ratio MAA to 0.43% HEMA | Volume of Safranine O solution adsorbed per gram, cc |
|---|---|---|
| 167 | 0.25 | 37.2 |

TABLE 13

| Example No. | Ratio MAA to 0.43% HEMA | Average platelet recovery, % |
|---|---|---|
| 168 | .064 | 81.5 |
| 169 | 0.13 | 86.2 |
| 170 | 0.19 | 87.8 |
| 171 | 0.25 | 80.6 |

We claim:

1. A device for the depletion of the leucocyte content of a platelet concentrate comprising a porous, fibrous medium having a CWST of at least about 90 dynes/cm.

2. The device of claim 1 in which said medium has a CWST of at least about 95 dynes/cm.

3. The device of claim 1 in which the fibers of the medium have been modified so as to present hydroxyl groups when immersed in an aqueous fluid.

4. The device of claim 3 in which the fibers have been modified by exposure to an energy source while in contact with a monomer comprising a polymerizable group and a hydroxyl-containing group.

5. The device of claim 4 in which the polymerizable group comprises an acrylic or methacrylic moiety.

6. The device of claim 4 in which the hydroxyl-containing group is hydroxyethyl.

7. The device of claim 4 in which said monomer is hydroxyethyl methacrylate.

8. The device of claim 1 in which the fibers of the medium have been modified to present hydroxyl groups together with a lesser number of a second anionic group.

9. The device of claim 8 in which the second anionic group is carboxyl.

10. The device of claim 8 in which the fibers of the medium have been modified by exposure to a monomer containing a polymerizable group and a carboxyl-containing group.

11. The device of claim 10 in which the polymerizable group comprises an acrylic or methacrylic moiety.

12. The device of claim 11 in which the polymerizable group and the carboxyl-containing group comprise the monomer, methacrylic acid.

13. The device of claim 12 in which the fibers of the medium have been modified with a mixture of monomers comprising methacrylic acid and hydroxyethyl methacrylate.

14. The device of claim 13 in which the acid/acrylate monomer weight ratio in the modifying mixture is between 0.01:1 to 0.5:1.

15. The device of claim 14 in which the concentration of hydroxyethyl methacrylate in the modifying mixture exceeds 0.1%.

16. The device of claim 15 in which the concentration of hydroxyethyl methacrylate in the modifying mixture exceeds 0.2%.

17. The device of claim 16 in which the concentration of hydroxyethyl methacrylate in the modifying mixture exceeds 0.4%.

18. The device of claim 17 in which the concentration of hydroxyethyl methacrylate in the modifying mixture is in the range of from about 0.2 to about 0.7%.

19. The device of claim 13 in which the acid monomer weight ratio is between 0.5:1 to 0.35:1.

20. The device of claim 12 in which the modification has been carried out using a grafting solution containing 2 to 10% of tertiary butyl alcohol.

21. The device of claim 20 in which the grafting solution contains about 4 to 5% of tertiary butyl alcohol.

22. The device of claim 12 in which the modification has been carried out using a grafting solution containing sufficient water soluble alcohol, or alcohol-ether to reduce its surface tension to less than about 40 dynes/cm.

23. The device of claim 22 in which the alcohol-ether is diethylene glycol monobutyl ether or ethylene glycol monobutyl ether.

24. The device of claim 1 in which at least one element of the porous medium has been preformed prior to assembly into a housing.

25. The device of claim 24 in which the preformed element comprises organic fibers less than about 30 micrometers in diameter.

26. The device of claim 1 in which the pore diameter exceeds about 3 micrometers.

27. The device of claim 1 in which the pore diameter exceeds about 3.4 micrometers.

28. The device of claim 1 in which the pore diameter exceeds about 3.8 micrometers.

29. The device of claim 1 in which the pore diameter is in the range of from about 3.8 to about 6 micrometers.

30. The device of claim 29 in which the bulk density of the medium is less than 0.36 grams/cc.

31. The device in accordance with claim 1 for use with a pooled lot of six to ten units of platelet concentrate each of about 50 to 70 ml in volume and in which the effective flow area exceeds 40 square centimeters.

32. The device of claim 31 in which the effective flow area exceeds 50 square centimeters.

33. The device of claim 32 in which the effective flow area exceeds 60 square centimeters.

34. A device in accordance with claim 1 for use with a single unit of 50 to 70 ml of platelet concentrate, in which the effective flow area exceeds about 6 square centimeters.

35. The device of claim 1 in which said medium is an element and said device further comprises a housing designed to accept the element and in which the external dimensions of the element are larger in lateral dimension than the matching housing internal lateral dimensions.

36. The device of claim 35 in which the element has the form of a right circular disc.

37. The device of claim 1 in which the porous medium has been preformed to form a preformed element of controlled pore diameter prior to assembly into a housing.

38. The device of claim 37 in which the preformed element has been shaped or sized by compression in a softened state.

39. The device of claim 1 in which a span between the upper and lower values used to define CWST is about 5 or fewer dynes/cm.

40. The device of claim 1 in which the FSA of the fibrous medium is at least 2.5 $M^2$.

41. The device of claim 1 in which the FSA of the fibrous medium is greater than 3.0 M².

42. The device of claim 1 in which the FSA of the fibrous medium is greater than 3.8 M².

43. The device of claim 1 in which the FSA of the fibrous medium is from about 2.5 to about 4.0 M².

44. The device of claim 1 in which the FSA of the fibrous medium is from about 3.3 to about 4.0 M².

45. A device for the depletion of the leucocyte content of a platelet concentrate comprising a porous medium having a CWST of at least about 90 dynes/cm and pore diameters in the range of from about 3.8 to about 6 micrometers.

46. A device for the depletion of the leucocyte content of platelet concentrate comprising a modified, porous, fibrous medium having a CWST of at least about 95 dynes/cm, a pore diameter in the range of from about 3.8 to about 6 micrometers, and a bulk density of less than 0.36 grams/cc, the fibers of said medium comprising polybutylene terephthalate and having diameters of less than 30 micrometers, the medium having an effective flow rate in excess of 40 square centimeters and the modification of the medium having been effected by the use of a mixture of methacrylic acid and hydroxyethyl methacrylate in which the acid/acrylate monomer weight ratio is between 0.05:1 to 0.35:1.

47. A method for the depletion of the leucocyte content of platelet concentrate comprising passing the platelet concentrate through the device in claim 1.

48. A method for the depletion of the leucocyte content of platelet concentrate comprising passing the platelet concentrate through the device of claim 2.

49. A method for the depletion of the leucocyte content of platelet concentrate comprising passing the platelet concentrate through the device of claim 3.

50. A method for the depletion of the leucocyte content of platelet concentrate comprising passing the platelet concentrate through the device of claim 4.

51. A method for the depletion of the leucocyte content of platelet concentrate comprising passing the platelet concentrate through the device of claim 5.

52. A method for the depletion of the leucocyte content of platelet concentrate comprising passing the platelet concentrate through the device of claim 6.

53. A method for the depletion of the leucoctye content of platelet concentrate comprising passing the platelet concentrate through the device of claim 7.

54. A method for the depletion of the leucocyte content of platelet concentrate comprising passing the platelet concentrate through the device of claim 8.

55. A method for the depletion of the leucocyte content of platelet concentrate comprising passing the platelet concentrate through the device of claim 9.

56. A method for the depletion of the leucocyte content of platelet concentrate comprising passing the platelet concentrate through the device of claim 10.

57. A method for the depletion of the leucocyte content of platelet concentrate comprising passing the platelet concentrate through the device of claim 11.

58. A method for the depletion of the leucocyte content of platelet concentrate comprising passing the platelet concentrate through the device of claim 12.

59. A method for the depletion of the leucocyte content of platelet concentrate comprising passing the platelet conentrate through the device of claim 13.

60. A method for the depletion of the leucocyte content of platelet concentrate comprising passing the platelet concentrate through the device of claim 14.

61. A method for the depletion of the leucocyte content of platelet concentrate comprising passing the platelet concentrate through the device of claim 15.

62. A method for the depletion of the leucoctye content of platelet concentrate comprising passing the platelet concentrate through the device of claim 16.

63. A method for the depletion of the leucocyte content of platelet concentrate comprising passing the platelet concentrate through the device of claim 17.

64. A method for the depletion of the leucocyte content of platelet concentrate comprising passing the platelet concentrate through the device of claim 18.

65. A method for the depletion of the leucocyte content of platelet concentrate comprising passing the platelet concentrate through the device of claim 19.

66. A method for the depletion of the leucocyte content of platelet concentrate comprising passing the platelet concentrate through the device of claim 20.

67. A method for the depletion of the leucocyte content of platelet concentrate comprising passing the platelet concentrate through the device of claim 21.

68. A method for the depletion of the leucocyte content of platelet concentrate comprising passing the platelet concentrate through the device of claim 22.

69. A method for the depletion of the leucocyte content of platelet concentrate comprising passing the platelet concentrate through the device of claim 23.

70. A method for the depletion of the leucocyte content of platelet concentrate comprising passing the platelet concentrate through the device of claim 24.

71. A method for the depletion of the leucocyte content of platelet concentrate comprising passing the platelet concentrate through the device of claim 25.

72. A method for the depletion of the leucocyte content of platelet concentrate comprising passing the platelet concentrate through the device of claim 26.

73. A method for the depletion of the leucocyte content of platelet concentrate comprising passing the platelet concentrate through the device of claim 27.

74. A method for the depletion of the leucocyte content of platelet concentrate comprising passing the platelet concentrate through the device of claim 28.

75. A method for the depletion of the leucocyte content of platelet concentrate comprising passing the platelet concentrate through the device of claim 29.

76. A method for the depletion of the leucocyte content of platelet concentrate comprising passing the platelet concentrate through the device of claim 30.

77. A method for the depletion of the leucocyte content of platelet concentrate comprising passing the platelet concentrate through the device of claim 31.

78. A method for the depletion of the leucocyte content of platelet concentrate comprising passing the platelet concentrate through the device of claim 32.

79. A method for the depletion of the leucocyte content of platelet concentrate comprising passing the platelet concentrate through the device of claim 33.

80. A method for the depletion of the leucocyte content of platelet concentrate comprising passing the platelet concentrate through the device of claim 34.

81. A method for the depletion of the leucocyte content of platelet concentrate comprising passing the platelet concentrate through the device of claim 35.

82. A method for the depletion of the leucocyte content of platelet concentrate comprising passing the platelet concentrate through the device of claim 36.

83. A method for the depletion of the leucocyte content of platelet concentrate comprising passing the platelet concentrate through the device of claim 37.

84. A method for the depletion of the leucocyte content of platelet concentrate comprising passing the platelet concentrate through the device of claim 38.

85. A method for the depletion of the leucocyte content of platelet concentrate comprising passing the platelet concentrate through the device of claim 39.

86. A method for the depletion of the leucocyte content of platelet concentrate comprising passing the platelet concentrate through the device of claim 40.

87. A method for the depletion of the leucocyte content of platelet concentrate comprising passing the platelet concentrate through the device of claim 41.

88. A method for the depletion of the leucocyte content of platelet concentrate comprising passing the platelet concentrate through the device of claim 42.

89. A method for the depletion of the leucocyte content of platelet concentrate comprising passing the platelet concentrate through the device of claim 43.

90. A method for the depletion of the leucoctye content of platelet concentrate comprising passing the platelet concentrate through the device of claim 44.

91. A method for the depletion of the leucocyte content of platelet concentrate comprising passing the platelet concentrate through the device of claim 45.

92. A method for the depletion of the leucocyte content of platelet concentrate comprising passing the platelet concentrate through the device of claim 46.

93. A method for the depletion of the leucocyte content of platelet concentrate comprising passing the platelet concentrate through a porous medium having a CWST of at least 90 dynes/cm.

94. A method for the depletion of the leucocyte content of platelet concentrate comprising passing the platelet concentrate through a device comprising a modified, porous, fibrous medium having a CWST of at least about 95 dynes/cm, a pore diameter in the range of from 3.8 to about 6 micrometers, and a bulk density of less than 0.36 grams/cc, the fibers of said medium comprsising polybutylene terephthalate and having diameters of less than 30 micrometers, the medium having an effective flow area in excess of 40 square centimeters and the modification of the medium having been effected by the use of a mixture of methacrylic acid and hydroxyethyl methacrylate in which the acid/acrylate monomer weight ratio is between 0.05:1 to 0.35:1.

* * * * *